US009747789B2

(12) United States Patent
Griswold et al.

(10) Patent No.: US 9,747,789 B2
(45) Date of Patent: Aug. 29, 2017

(54) MAGNETIC RESONANCE IMAGING WITH SWITCHED-MODE CURRENT-SOURCE AMPLIFIER HAVING GALLIUM NITRIDE FIELD EFFECT TRANSISTORS FOR PARALLEL TRANSMISSION IN MRI

(71) Applicant: Case Western Reserve University, Cleveland, OH (US)

(72) Inventors: Mark Griswold, Shaker Heights, OH (US); Michael Twieg, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 821 days.

(21) Appl. No.: 14/053,144

(22) Filed: Oct. 14, 2013

(65) Prior Publication Data

US 2014/0292327 A1    Oct. 2, 2014

Related U.S. Application Data

(60) Provisional application No. 61/806,907, filed on Mar. 31, 2013.

(51) Int. Cl.
*G01V 3/00* (2006.01)
*G08C 23/06* (2006.01)
(Continued)

(52) U.S. Cl.
CPC ............ *G08C 23/06* (2013.01); *A61B 5/0017* (2013.01); *A61B 5/0073* (2013.01);
(Continued)

(58) Field of Classification Search
CPC ............ G01R 33/3614; G01R 33/3692; G01R 33/4822; G01R 33/56; G01R 33/5608;
(Continued)

(56) References Cited

U.S. PATENT DOCUMENTS 5,296,813 A * 3/1994 Holmes ............ G01R 33/34007
324/318
5,406,192 A * 4/1995 Vinciarelli .......... H02M 1/4225
323/222

(Continued)

OTHER PUBLICATIONS

Yang et al., Investigation Non-magnetic Amplifiers Applied in an MRI System, 2010, Proc. Intl. Soc. Mag. Reson. Med. 18.*

(Continued)

*Primary Examiner* — Susan Lee
(74) *Attorney, Agent, or Firm* — Quarles & Brady LLP; Jack Cook

(57) ABSTRACT

Example systems, apparatus, circuits, and other embodiments described herein concern parallel transmission in MRI. One example apparatus includes at least two enhanced mode gallium nitride (eGaN) based field effect transistors (FETs) that are connected by a coil that includes an LC (inductance-capacitance) leg. The apparatus includes a controller that inputs a signal to the eGaN FETs to control the production of an output analog radio frequency (RF) signal. The LC leg selectively alters the output analog RF signal. The analog RF signal is used in parallel magnetic resonance imaging (MRI) transmission. One embodiment provides an MRI transmit coil with switched-mode current-source amplification provided by a gallium nitride FET.

57 Claims, 19 Drawing Sheets

(51) Int. Cl.
G01R 33/36 (2006.01)
G01R 33/56 (2006.01)
G01R 33/48 (2006.01)
G01R 33/58 (2006.01)
A61K 49/06 (2006.01)
A61B 5/00 (2006.01)
G01R 33/563 (2006.01)
A61B 5/055 (2006.01)

(52) U.S. Cl.
CPC ............ *A61B 5/4244* (2013.01); *A61K 49/06* (2013.01); *G01R 33/3614* (2013.01); *G01R 33/3692* (2013.01); *G01R 33/4822* (2013.01); *G01R 33/56* (2013.01); *G01R 33/5608* (2013.01); *G01R 33/56366* (2013.01); *G01R 33/58* (2013.01); *A61B 5/055* (2013.01)

(58) Field of Classification Search
CPC G01R 33/56366; G01R 33/58; A61B 5/0017; A61B 5/0073; A61B 5/4244; A61B 5/055; A61K 49/06
USPC .......................................................... 324/309
See application file for complete search history.

(56) References Cited

U.S. PATENT DOCUMENTS

| | | | | |
|---|---|---|---|---|
| 5,445,162 A * | 8/1995 | Ives | ................... | G01R 33/5673 600/413 |
| 6,256,482 B1 * | 7/2001 | Raab | ..................... | H03F 1/0227 330/199 |
| 7,622,925 B2 * | 11/2009 | Fujimoto | ........... | G01R 33/3415 324/309 |
| 7,671,595 B2 * | 3/2010 | Griswold | ........... | G01R 33/3415 324/318 |
| 2006/0068697 A1 * | 3/2006 | Tanabe | .................. | H03F 1/0244 455/1 |
| 2010/0246153 A1 * | 9/2010 | Buer | ....................... | H01L 23/66 361/784 |
| 2010/0253351 A1 * | 10/2010 | Huish | .............. | G01R 33/34007 324/318 |
| 2014/0070808 A1 * | 3/2014 | Reykowski | ........ | G01R 33/3657 324/309 |

OTHER PUBLICATIONS

Lidow et al., Enhancement Mode Gallium Nitride (eGaN) FET Characteristics under Long Term Stress, Mar. 2011.*

Davis, Enhancement Mode Gallium Nitride MOSFET Delivers Impressive Performance, Mar. 2010, Power Electronics.*

Efficient Power Conversion Development Board Demonstrates Ease of Designing Power Systems with 200 V eGaN FETS, Feb. 2013.*

* cited by examiner

MAGNETIC RESONANCE IMAGING WITH SWITCHED-MODE CURRENT-SOURCE AMPLIFIER HAVING GALLIUM NITRIDE FIELD EFFECT TRANSISTORS FOR PARALLEL TRANSMISSION IN MRI

PRIORITY CLAIM

This application claims the benefit of U.S. Provisional Patent Application 61/806,907 titled "Medical Imaging", filed Mar. 31, 2013.

BACKGROUND

Magnetic resonance imaging (MRI), nuclear magnetic resonance (NMR), and other magnetic resonance (MR) systems continue to become more sophisticated, powerful, precise, and complicated. MR systems rely on transmit coils to expose volumes to precisely controlled radio frequency (RF) energy. Like the larger overall MR system, RF transmit coils also continue to become more sophisticated, powerful, and complicated.

RF transmit systems continue to add more independent elements to correct B1 inhomogeneity, to reduce the specific absorption rate (SAR) at high field strengths (e.g., 3 T, 7 T), or for other reasons. However, adding more independent elements can be complicated by factors including inter-element coupling, cabling restrictions, and other factors. Element and coil design is further complicated by the unique and intense environment (e.g., 7 T magnetic field, rapid gradient switching, complex RF pulse sequences) in which RF transmit coils operate.

MR involves the transmission of RF energy. RF energy used to produce MR may be transmitted by a coil. Resulting MR signals may also be received by a coil. In early MRI, RF energy may have been transmitted from a single coil and resulting MR signals received by a single coil. Later, multiple receivers may have been used in parallel acquisition techniques. Using multiple receivers facilitates speeding up signal reception, which in turn may reduce scan time. Similarly, multiple transmitters may be used in parallel transmission techniques. Using multiple transmitters may facilitate speeding up a transmission process, which in turn may facilitate volumetric excitation, selective isolation, and other very high speed features. However, conventional parallel transmission techniques have encountered issues with scaling, fidelity, and synchronization.

Conventional systems may have relied on multiple, individually powered, single channel, analog-in-analog-out RF transmitters for parallel transmission. These systems tended not to scale well due to cabling duplication, power transmitter duplication, control duplication, and other issues. Even when a small number (e.g., 4) of transmitters were employed, these systems may not have produced desired fidelity. Additionally, conventional systems typically had poor isolation between coils, resulting in degraded performance.

Conventional systems may also have been limited by their use of relatively low power (e.g., <50 W), low efficiency class A or class AB amplifiers. While some systems may have included on-coil series and/or shunt-fed class-D amplifiers, even these conventional systems suffered from several limitations including inadequate detuning and low efficiency. Due, at least in part, to these limitations, conventional systems may not have produced desired levels of amplitude and/or phase control and thus may have had less than desirable fidelity.

Some RF transmit coils were therefore designed using a transmit amplifier on the transmit coil. Some RF transmit coils may even have used high efficiency amplifier topologies. While these approaches have led to improvements, designing circuits that include amplifiers is still constrained by factors including amplifier size, heat dissipation, and other factors.

The field of coil design using on-coil switched-mode amplifiers for parallel transmission is relatively new. For example, U.S. Pat. No. 7,671,595, which issued on Mar. 2, 2010 to one of these same inventors, presented an early on-coil switched-mode amplifier. U.S. Pat. No. 7,671,595 ("the '595 patent) is entitled "On-coil Switched-mode Amplifier for Parallel Transmission in MRI" and describes an on-coil current-mode class-D (CMCD) amplifier that may be used to produce MRI transmission-coil excitations at desired RF frequencies. The on-coil CMCD amplifier is capable of performing within or proximate to the bore of the MRI magnet or within less than one wavelength of the RF signal produced by the transmit coil or at other positions or locations. Providing an on-coil amplifier allows digital control signals to be sent to the coil assembly, improving synchronization between the transmission-coils while reducing interference, cross talk, physical space requirements associated with cables, and heating normally associated with parallel transmission MRI systems. The on-coil CMCD amplifier described in the '595 patent may be driven by signals produced by one or more linear pre-amplifiers.

Once this type of coil had been built, additional research using the new on-coil switched-mode amplifier revealed the need for further refinements including those presented in U.S. Pat. No. 8,294,464, which issued on Oct. 23, 2012 to one of these same inventors and in U.S. Pat. No. 8,294,465, which also issued on Oct. 23, 2012 to one of these same inventors. These patents describe improvements to the on-coil switched-mode amplifiers including the use of CMCD amplifiers, switched-mode pre-amplification, and amplitude modulation (AM) feedback for the on-coil switched-mode amplifiers. Once again, as these on-coil switched-mode amplifiers were built and used, further research revealed the need for further optimizations.

BRIEF DESCRIPTION OF THE DRAWINGS

The accompanying drawings, which are incorporated in and constitute a part of the specification, illustrate various example systems, methods, and other embodiments of various aspects of the invention. It will be appreciated that the illustrated element boundaries (e.g., boxes, groups of boxes, or other shapes) in the figures represent one example of the boundaries. One of ordinary skill in the art will appreciate that in some embodiments one element may be designed as multiple elements, multiple elements may be designed as one element, an element shown as an internal component of another element may be implemented as an external component and vice versa, and so on. Furthermore, elements may not be drawn to scale.

DETAILED DESCRIPTION

Example apparatus, methods, and other embodiments replace a conventional FET (e.g., silicon (Si) field effect transistor (FET), laterally diffused metal oxide semiconductor (LDMOS) RF FET) on an on-coil amplifier with an enhancement mode gallium nitride (eGaN) FET. The eGaN FET based switched-mode amplifier facilitates improving efficiency over conventional systems while reducing amplifier footprint and cost.

Figure 1:
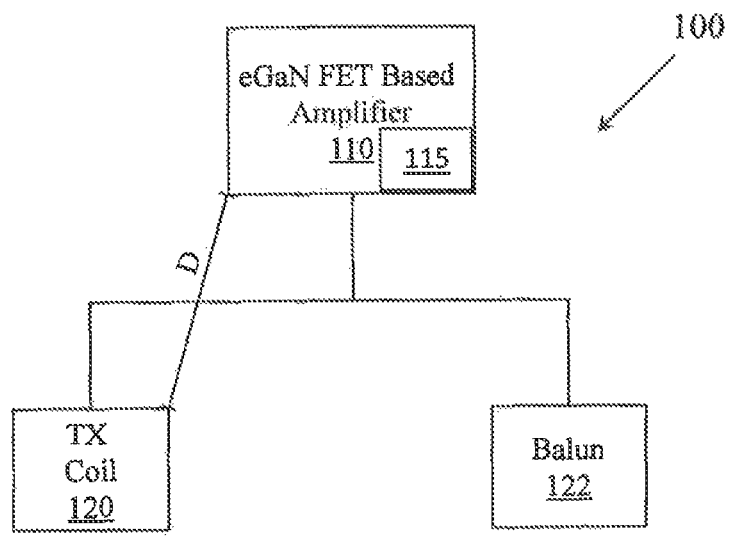
FIG. 1 illustrates a portion of an MR apparatus that includes an MR transmit coil controlled, at least in part, by a switched-mode current-source amplifier having enhanced mode gallium nitride (eGaN) FETs.
Figure 2:
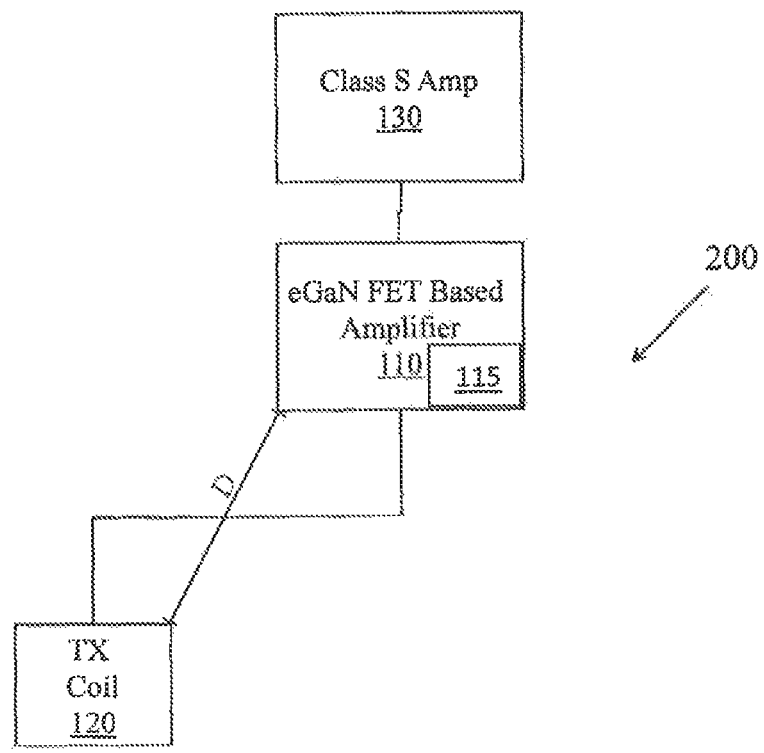
FIG. 2 illustrates a portion of an MR apparatus that includes an MR transmit coil controlled, at least in part, by a switched-mode current-source amplifier having gallium nitride FETs.
Figure 3:
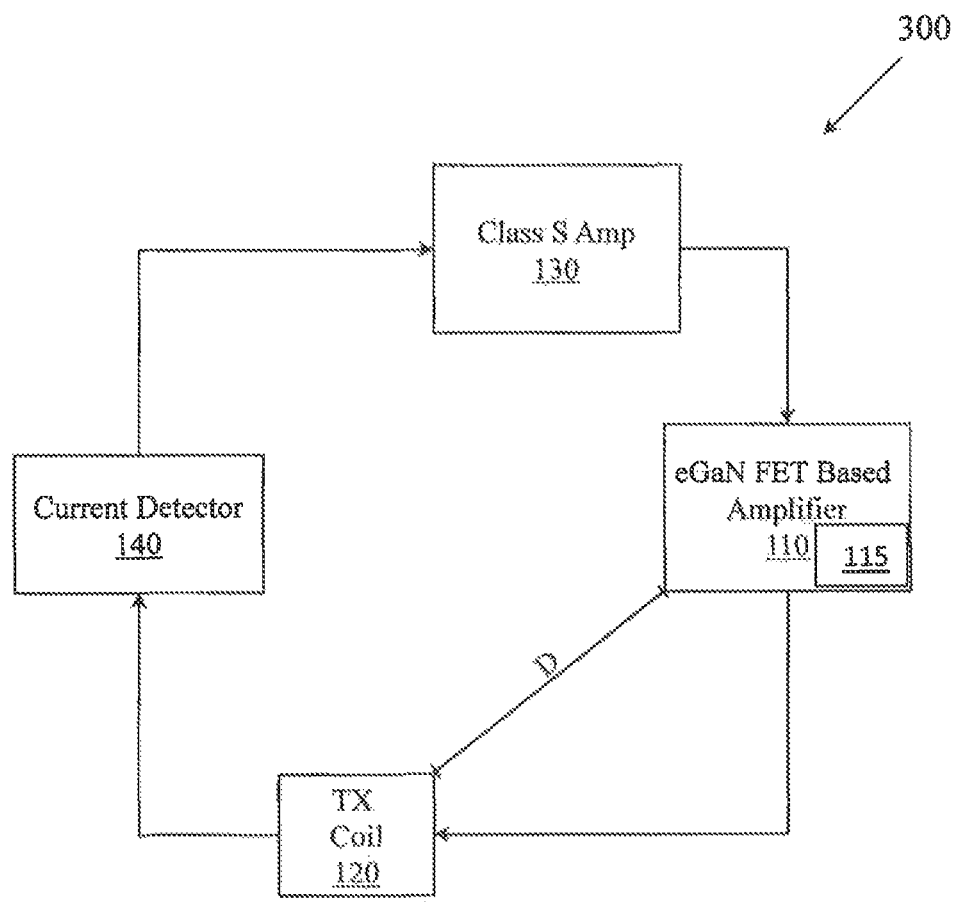
FIG. 3 illustrates a portion of an MR apparatus that includes an MR transmit coil controlled, at least in part, by a switched-mode current-source amplifier having gallium nitride FETs.

FIG. 1 illustrates a portion 100 of an apparatus that includes an MR transmit coil 120 being driven by a switched-mode current-source amplifier 110 having gallium nitride FETs. The switched-mode current-source amplifier 110 may be used to drive the transmit coil 120. The amplifier 110 may also be used to drive a load via a balun 122. Balun 122 may be, for example a 50Ω balun. The apparatus may also include a transmit module 115 that performs envelope elimination and restoration (EER). Performing EER may allow the amplifier 110 to replicate shaped RF pulses produced by an MR apparatus. FIG. 1-3 illustrate a distance D between the amplifier 110 and the MR transmit coil 120. In one embodiment, distance D may be 1 centimeter or less. The amplifier 110 may be configured to be within 1 centimeter of a bore of an MR apparatus. In another embodiment, distance D may be 2 meters or less. The amplifier 110 may be configured to be within 2 meters of a bore of an MR apparatus.

FIG. 2 illustrates a portion 200 of an apparatus that includes an MR transmit coil 120 being driven by a switched-mode current-source amplifier 110 having gallium nitride FETs. The switched-mode current-source amplifier 110 may receive a supply voltage from, for example, a class S amplifier 130. Like amplifier 110 may include eGaN FETs instead of conventional Si FETs, so too may class S amplifier 130 include eGaN FETs instead of conventional FETs. In one example, the efficiency of the class S amplifier is at least 90%. The apparatus may also include a transmit module 115 that performs envelope elimination and restoration (EER). Performing EER may allow the amplifier 110 to replicate shaped RF pulses produced by an MR apparatus. The transmit module 115 is connected to the amplifier 110.

FIG. 3 illustrates a portion 300 of an apparatus that includes MR transmit coil 120 being driven by a switched-mode current-source amplifier 110 having gallium nitride FETs. The switched-mode current-source amplifier 110 may receive a supply voltage from, for example, class S amplifier 130. In this embodiment, the current on transmit coil 120 can be detected by, for example, a current detector 140. One skilled in the art will appreciate that various circuits or elements may be configured as a current detector 140. Since the current on transmit coil 120 can be detected by current detector 140, in one embodiment the current output from amplifier 110 can be modulated by, for example, varying the supply voltage to the amplifier 110. In one embodiment, the supply voltage may be modulated using the class S amplifier 130. The class S amplifier 130 may in turn have its operation controlled, at least in part, by current detector 140. Using eGaN FETs provide several advantages over conventional FETs. In one embodiment, a transmit module 115 performs envelope elimination and restoration (EER). Performing EER may allow the amplifier 110 to replicate shaped RF pulses produced by an MR apparatus. The Transmit module 115 is connected to amplifier 110.

In 2013, an Si LDMOS FET with a 300 W power output may have cost N dollars. An Si LDMOS FET with a 10 W output may have cost N/4 dollars. However, an eGaN FET with a 15 W output may have cost only N/30 dollars. Additionally, the eGaN FET may have been much smaller (e.g., $1/500^{th}$) than conventional FETs. For example, an eGaN FET may have been 2 mm$^2$ while a conventional FET may have been 1000 mm$^2$. An example smaller and less expensive eGaN FET from Efficient Power Conversion Corporation may exhibit substantially similar state resistance and breakdown voltage when compared to a larger, more expensive conventional LDMOS RF FET. In one embodiment, an eGaN FET with a lateral high electron mobility transistor (HEMT) structure may provide junction capacitances of approximately 250 pF while providing high frequency (e.g., 63.6 MHz) operation.

Even with these cost, size, and performance characteristics, eGaN FETs were not previously used in the switched-mode on-coil amplifier application. Perhaps because eGaN FETs may originally have been intended for DC-DC power conversion applications, which have historically not been a significant issue in coil design. Additionally, the field of switched-mode on-coil amplifiers only developed very recently, as chronicled in the background section. Thus, the problems solved and the optimizations provided by using eGaN FETs on switched-mode on-coil amplifiers for MRI transmission coils did not exist until the field of switched-mode on-coil amplifiers came into existence.

Once the on-coil switched-mode amplifier for MRI transmit coils was invented, the need arose for pre-amplification (U.S. Pat. No. 8,294,465) and for the use of improved (e.g., current mode class D amplifiers) (U.S. Pat. No. 8,294,464). Once these refinements to on-coil switched-mode amplifiers for MRI transmit coils were available, work could proceed on further optimizing performance, design, cost, safety, and other factors. Thus, even though eGaN FETs may originally have been used for DC-DC power conversion applications, eGaN FETs provide improvements in on-coil or near-coil switched-mode amplifiers operating at frequencies that are relevant to MRI scanners.

In one embodiment, in addition to improving the on-coil amplification stage by using eGaN FETs, example apparatus may include a transmit module that performs envelope elimination and restoration (EER). Performing EER allows the improved on-coil eGaN FET based amplifier to replicate shaped RF pulses produced by an MR scanner.

Figure 4:
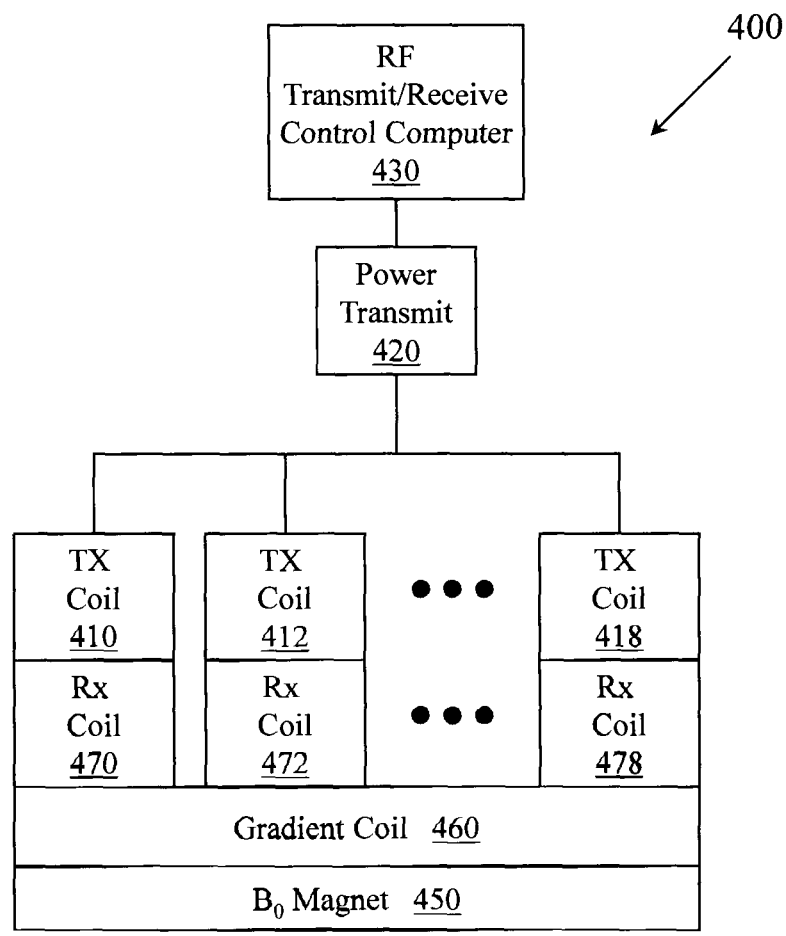
FIG. 4 illustrates portions of a parallel MR apparatus configured with an on-coil switched-mode amplifier.

FIG. 4 illustrates an example system 400 that uses multiple independent transmit coils (e.g., 410, 412 . . . 418) and multiple receive coils (e.g., 470, 472 . . . 478). The transmit coils have on-coil switched-mode amplifiers that facilitate improved parallel transmission in MRI. In one example, an "on-coil" amplifier is an amplifier that performs within the bore of a magnet in an MRI apparatus. One skilled in the art will appreciate that MRI apparatus are generally enclosed in a bounding Faraday cage. In another example, an "on-coil" amplifier is an amplifier that performs near the bore of the magnet, yet still within the volume of space enclosed by a bounding Faraday cage. In yet another example, an "on-coil" amplifier is an amplifier that performs within a distance from the transmit coil of less than one wavelength of the RF signal produced by the transmit coil. As used herein, "on-coil" refers to the position of the amplifier that includes the eGaN FET(s). In different embodiments, the on-coil amplifier may be placed on a circuit board that includes the transmit coil, may be placed within one millimeter of the transmit coil, may be placed within one centimeter of the transmit coil, may be placed within one meter of the transmit coil, may be placed within two meters of the transmit coil, or may be placed at other locations.

The transmit coils may be powered by digital controllers (e.g., power transmitters 420) that are controlled by a computer 430. Thus, synchronization may be improved over conventional systems. Using a single digital controller 420 may also reduce issues associated with physical layout, synchronization, heating, and cooling. The electronic components (e.g., eGaN FETs) in the on-coil switched-mode amplifier facilitate controlling the coils with a digital signal. Thus, the transmit coils may receive a digital signal and produce an analog signal having improved characteristics. Once again the system would also include other standard MRI apparatus elements (e.g., main field magnet 450, gradient coils 460).

Figure 5:
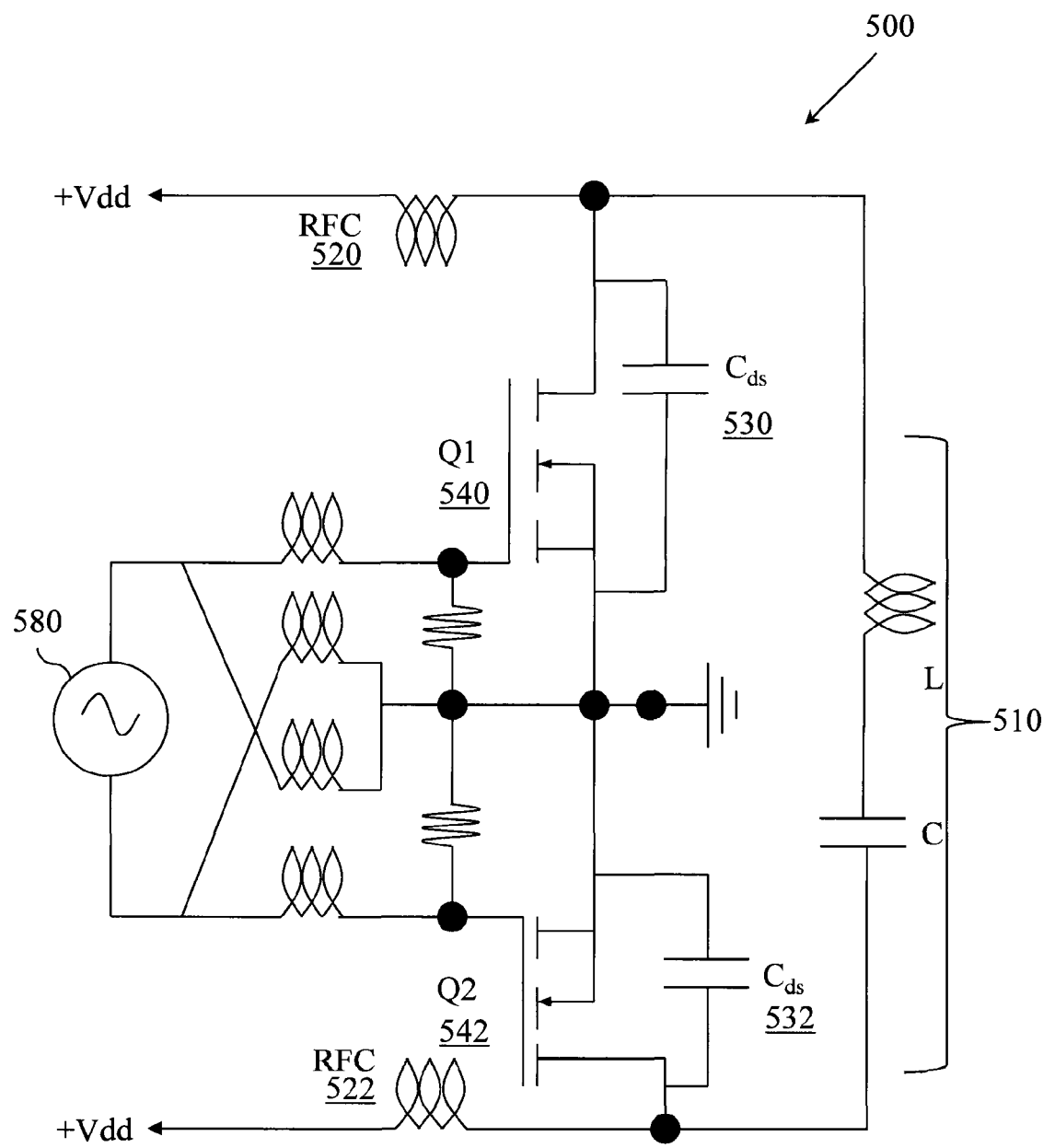
FIG. 5 illustrates a current-mode class-D amplifier topology for use in parallel MRI transmission involving on-coil switched-mode amplification.

FIG. 5 illustrates an example current-mode class-D amplifier topology 500. This topology may be referred to collectively as a CMCD amplifier. A coil configured with this topology may be referred to as an LC-switched-mode coil. In the illustration, the coil is represented by the series LC leg 510. The L refers to inductance in the coil 510 and the C refers to capacitance in the coil 510. The two chokes RFC (e.g., 520, 522) act as current-sources. The drain-source capacitances $C_{ds}$ (e.g., 530, 532) are in series with the coil 510. Alternative shunting of an applied DC voltage to ground when an FET is driven to saturation produces excitation at desired RF frequencies. Conventionally, the FETs (e.g., Q1 540, Q2 542) may have been large LDMOS RF FETs. Example apparatus employ eGaN FETs. In one example, element 580 corresponds to an RF transmission unit 1060 in FIG. 10. While LC Leg 510 is illustrated in one configuration in FIG. 5, it is to be appreciated that an LC leg may have different filter configurations and may include both parallel and serial components as well as combinations thereof.

Figure 8:
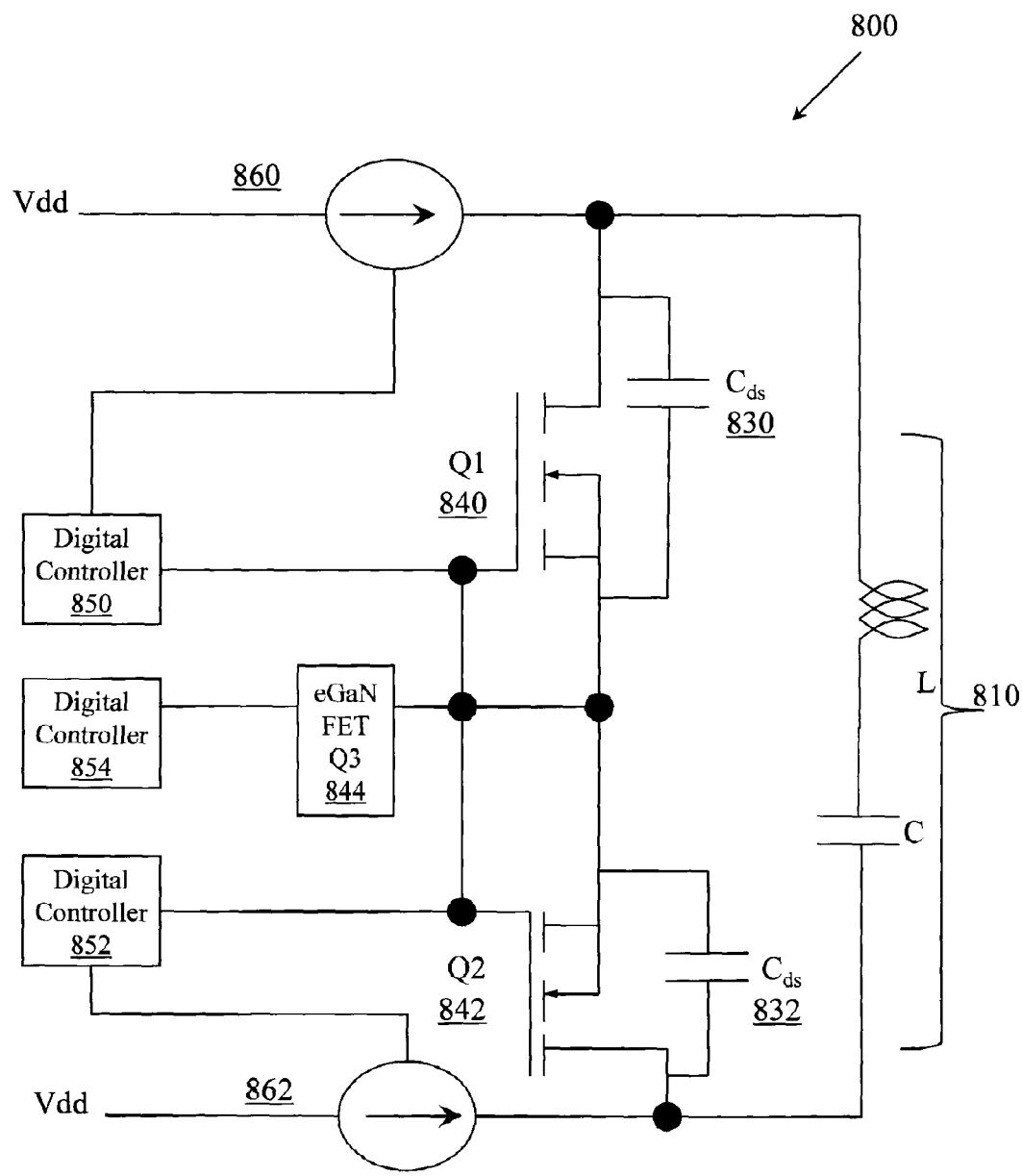
FIG. 8 illustrates a topology in which an additional eGaN FET has been added.

The example CMCD design may be implemented on or near an array of surface coils of various sizes (e.g., 8.5 cm×8.5 cm). The coils may include various shielding configurations (e.g., 12.5 cm×12.5 cm). The coils may be tuned to different field strengths (e.g., 1.5 T, 3 T, 7 T). In one embodiment, the coils may be single turn or multi-turn coils. Note that the terminals of coil 510 are attached between the drains of the two FETs (Q1 540, Q2 542) and tuned so that the circuit is series resonant when one of the FETs is switched on. In one example, both FETs may be driven out of phase to optimize efficiency. While two FETs (Q1 540, Q2 542) are illustrated, it is to be appreciated that two or more FETs may be employed. See, for example, system 800 (FIG. 8). Unlike a conventional circuit, the FETs (Q1 540, Q2 542) may be eGaN FETs.

Example systems improve on conventional apparatus by using eGaN FETs that can be driven by low power (e.g., 5V) signals. One example system (e.g., FIG. 5) uses a current-mode class-D (CMCD) amplifier topology. CMCD amplifiers may produce higher efficiency at higher output power than class-D or class-E amplifiers. The higher efficiency at higher output power is related to the series incorporation of eGaN FET drain source capacitance Cds in a coil loop, which facilitates zero voltage switching. In one example, a drain efficiency of the eGaN FETs is at least 85% when driving a 50 ohm load. In another example, a power added efficiency of the eGaN FETs is at least 85% when driving a 50 ohm load. The coil transmit current may be uniquely controlled by the gate voltage. Since the load may be driven directly by the amplifier (e.g., does not require tuning and matching to a 50 ohm network), the amplifier is referred to as a "current mode" amplifier. Since the current in the transmit coil is uniquely determined by the gate voltage, this suppresses coupled currents from other transmit coils.

Figure 6:
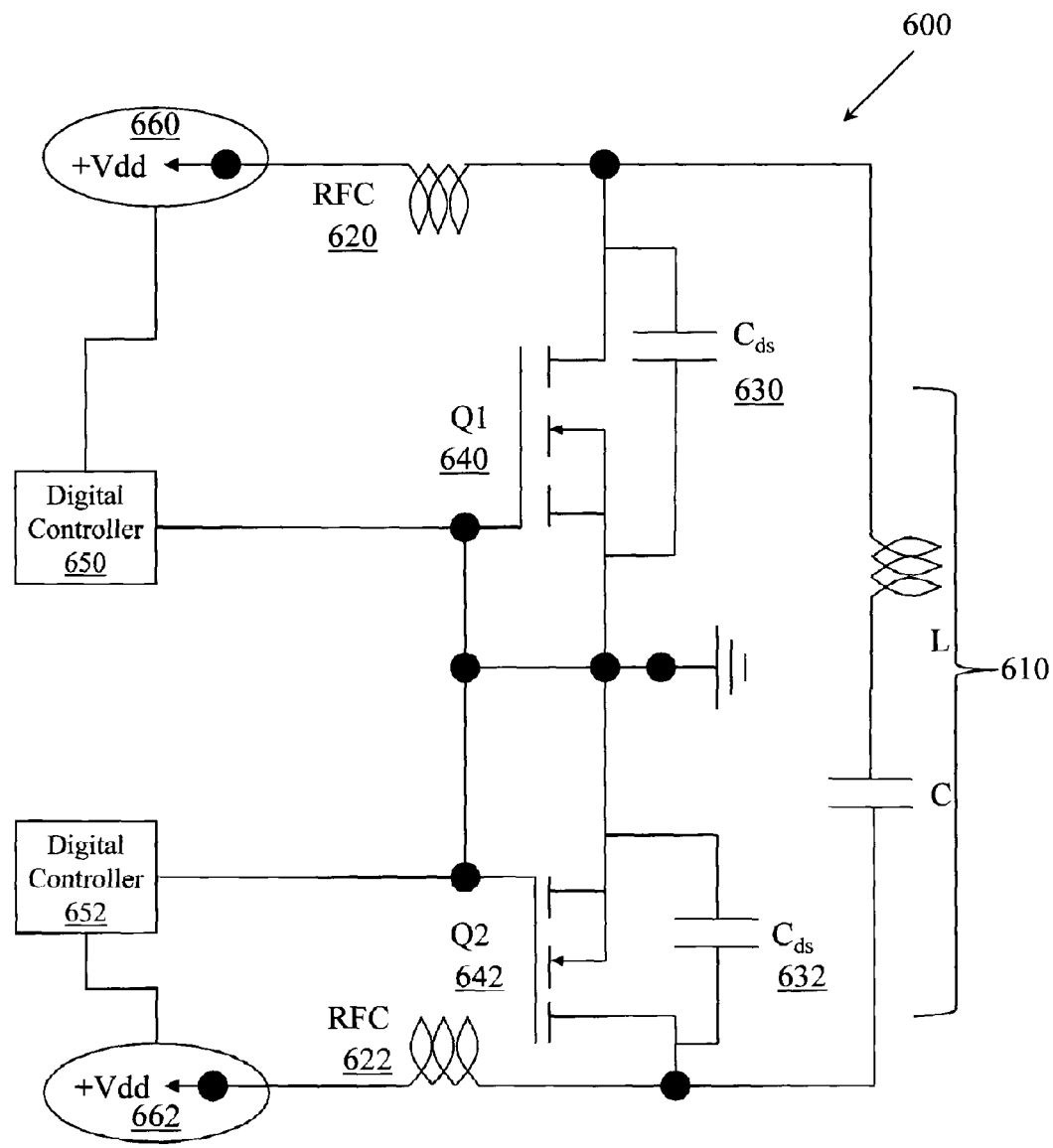
FIG. 6 illustrates a topology in which voltage and/or current-sources are additionally and/or alternatively digitally controllable.
Figure 7:
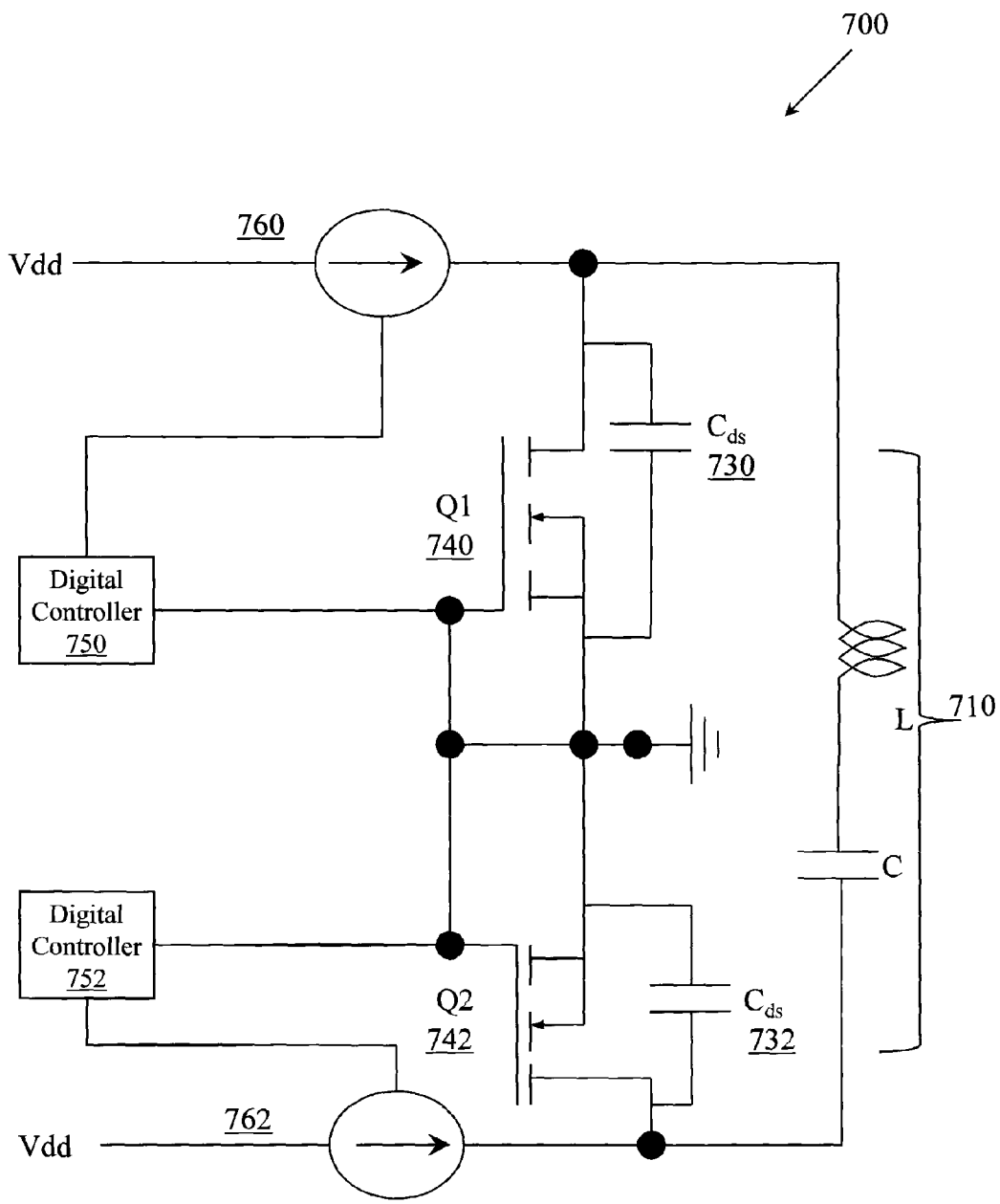
FIG. 7 illustrates a topology in which current-sources are additionally and/or alternatively digitally controllable.

It is to be appreciated that FIG. 5 is one example topology. FIGS. 6, 7, and 8 illustrate different examples and illustrate the additional and/or alternative digital control of current-sources and/or supplies. These figures generally describe an "on-coil" CMCD amplifier. "On-coil" may mean on the coil, near the coil, or within a certain distance of the coil. Since the amplifier is located on the coil, frequency matching is not required. This facilitates performing a one-time load-independent match for the amplifier. Since the amplifier is a class-D amplifier, a digital input can be employed.

Consider FIG. 6, which illustrates a topology 600 in which voltage and/or current-sources are additionally and/or alternatively digitally controllable. Topology 600 may be arranged, for example, as a circuit. FIG. 6 includes several elements similar to those described in connection with topology 500 (FIG. 5). For example, topology 600 includes an LC leg 610, two current-sources 620 and 622, two drain-source capacitances 630 and 632, and two FETs 640 and 642. Once again, FETs 640 and 642 may be eGaN FETs instead of conventional Si FETs. In addition to the digital control in FIG. 5, FIG. 6 illustrates a digital controller 650 and a digital controller 652. These digital controllers provide digital control of the {+Vdd, RFC} elements 660 and 662. This digital control facilitates improving amplitude modulation accuracy and ease of use.

More generally, FIG. 6 illustrates an apparatus having at least two eGaN FETs (e.g., 640, 642) connected by a coil

610 including an LC leg. In one example, the at least two eGaN FETs (e.g., 640, 642) drive a current in the coil 610 of at least 3 A RMS. In another example, the at least two eGaN FETs (e.g., 640, 642) drive a current in the coil 610 of at least 5 A RMS. The apparatus includes a controller (e.g., 650, 652) to input a digital signal to the at least two eGaN FETs (e.g., 640, 642) and to control the production of an output analog radio frequency (RF) signal, based, at least in part, on the digital signal. The LC leg 610 is to selectively alter the output analog RF signal. The output analog RF signal is associated with parallel MRI transmission. The apparatus also includes at least two drain-source capacitances (e.g., 630, 632) in series with the coil 610. In one example, the digital control signal provided by digital controller 650 and/or 652 may be determinable from the desired analog RF signal by sigma delta modulation, pulse width modulation, pulse train optimization, and so on. In one example, the digital control signal may be a voltage in the range of 0.1V to 50V and the output analog RF signal may have a power in the range of 1 W to 3000 W.

In one example, the digital controllers 650 and 652 are connected to the at least two eGaN FETs (e.g., 640, 642) by a dedicated connection. The dedicated connection may be, for example, a wireless connection, a fiber optic connection, and so on. While FIG. 6 illustrates a single apparatus 600, it is to be appreciated that multiple instances of the apparatus 600 may be implemented on an array of surface coils. These surface coils may be tuned to different field strengths and may include a shielding element.

FIG. 7 illustrates a topology 700 in which current-sources are additionally and/or alternatively digitally controllable. Topology 700 may be arranged, for example, as a circuit. FIG. 7 includes several elements similar to those described in connection with topology 600 (FIG. 6). For example, topology 700 includes an LC leg 710, two current-sources 760 and 762, two drain-source capacitances 730 and 732, two eGaN FETs 740 and 742, and two digital controllers 750 and 752. Note that the {+Vdd, RFC} elements 660 and 662 (FIG. 6) have been replaced with more generic current-sources 760 and 762, which are digitally controlled by digital controllers 750 and 752 respectively. Once again this digital control facilitates improving amplitude modulation accuracy and ease of use.

FIG. 8 illustrates a topology 800 in which an additional eGaN FET Q3 844 and an additional corresponding digital controller 854 have been added to the topology 700 illustrated in FIG. 7. Topology 800 may be arranged, for example, as a circuit. FET Q3 844 is illustrated using a labeled box rather than a conventional circuit drawing element. This is to point out that "FET", as used herein, is a generic term and may refer to class of switching elements that can be gallium nitride based and that may include, for example, FETs (field effect transistor), BJTs (bipolar junction transistor), JFETs (junction FET), or other switching elements. Thus, in different embodiments of the apparatus and circuits described herein, different eGaN based switching elements may be employed. FIG. 8 includes several elements similar to those described in connection with topology 700 (FIG. 7). For example, topology 800 includes an LC leg 810, current-sources 820 and 822, drain-source capacitances 830 and 832, eGaN FETs 840 and 842 (along with additional FET 844), digital controllers 850 and 852 (along with additional digital controller 854), and current-sources 860 and 862.

Figure 9:
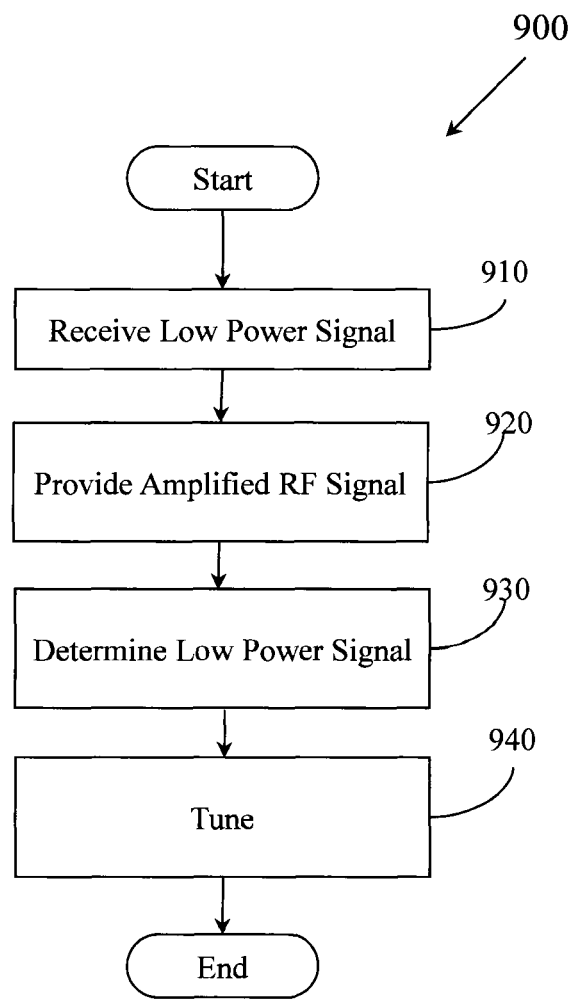
FIG. 9 illustrates a method associated with switched-mode current-source amplification.

FIG. 9 illustrates a method 900 associated with switched-mode current-source amplification. Method 900 includes, at 910, receiving a low power digital control signal associated with parallel transmission in MRI. The low power signal may be, for example, a 5V digital signal.

Method 900 also includes, at 920, controlling an MRI apparatus to provide an amplified analog RF signal for parallel transmission. In one embodiment, the analog RF signal is determined, at least in part, by the low power digital control signal. In one embodiment, providing the amplified analog RF signal includes providing the low power digital control signal to a gallium nitride field FET based on-coil current-mode amplifier, where the coil includes an LC leg.

Method 900 also includes, at 930, determining the low power digital control signal from the amplified analog RF signal by sigma delta modulation, pulse width modulation, or pulse train optimization. Method 900 also includes, at 940, receiving a tuning signal and selectively tuning a set of surface coils associated with the MRI apparatus to different operating frequencies based, at least in part, on the tuning signal.

Figure 10:
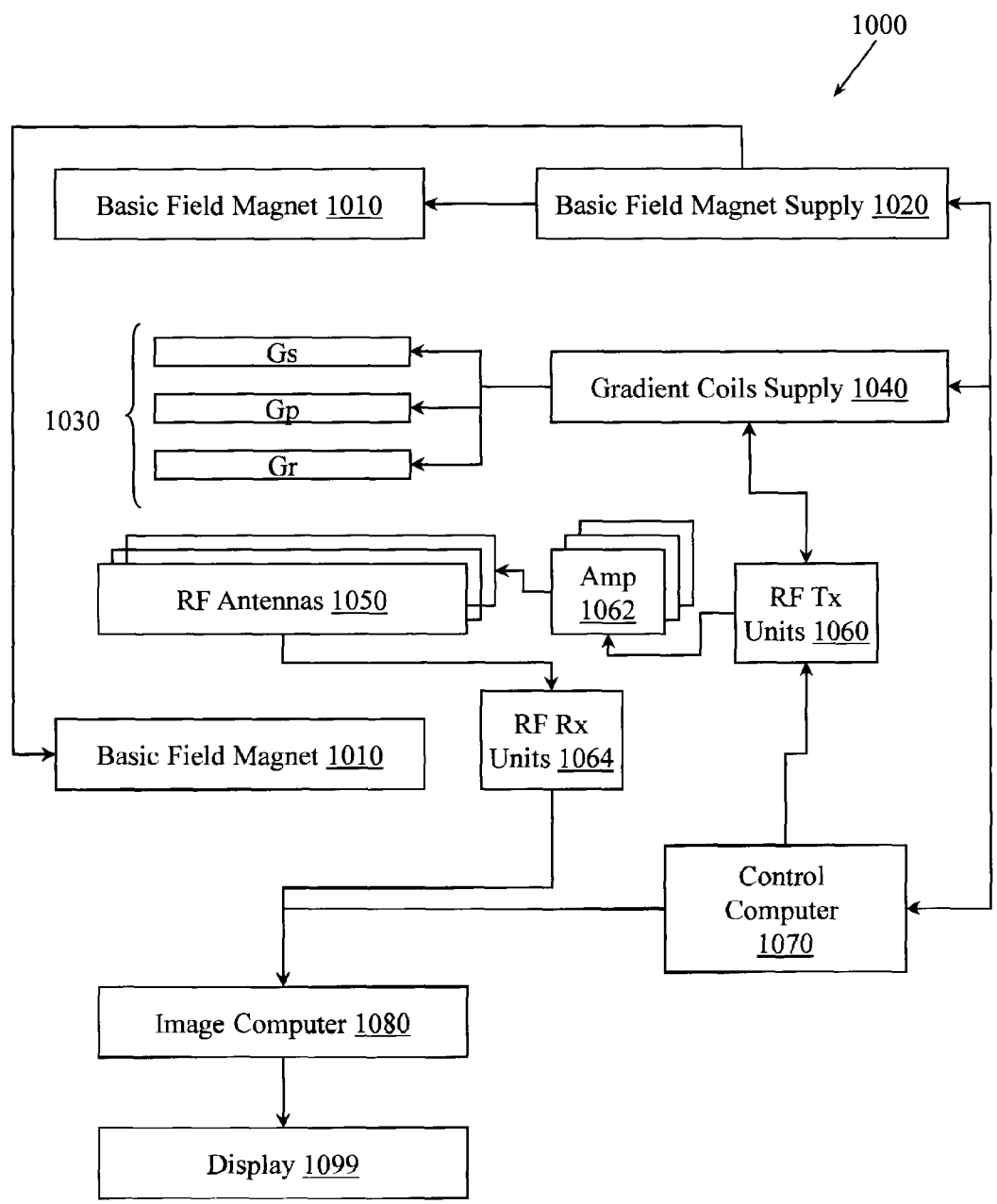
FIG. 10 illustrates an MRI apparatus configured with an on-coil switched-mode current-source amplifier having eGaN FETs.

FIG. 10 illustrates an example MRI apparatus 1000 configured with a set of on-coil switched-mode current-source amplifiers 1062 having eGaN FETs to facilitate improved parallel transmission of analog RF signals used in MRI. The on-coil switched-mode amplifiers 1062 may be configured like those illustrated in FIGS. 5 through 8 and in FIG. 11. In one embodiment, the eGaN FETs may be less than 2 mm$^2$ in area, while in another embodiment, the eGaN FETS may be less than 0.5 mm$^2$. Consider a relationship between elements in FIG. 5 and elements in FIG. 10. The RF antennas 1050 may correspond in part to element 510 (FIG. 5). The amplifiers 1062 may correspond in part to topology 500, minus elements 510 and 580. The RF transmission (TX) units 1060 may correspond to element 580. Similar correlations may be made between elements in FIGS. 6-8 and FIG. 11.

The apparatus 1000 includes a basic field magnet(s) 1010 and a basic field magnet supply 1020. Ideally, the basic field magnets 1010 would produce a uniform $B_0$ field. However, in practice, the $B_0$ field may not be uniform, and may vary over an object being imaged by the MRI apparatus 1000. MRI apparatus 1000 may include gradient coils 1030 configured to emit gradient magnetic fields like $G_S$, $G_P$ and $G_R$. The gradient coils 1030 may be controlled, at least in part, by a gradient coils supply 1040. In some examples, the timing, strength, and orientation of the gradient magnetic fields may be controlled, and thus selectively adapted, during an MRI procedure.

MRI apparatus 1000 may include a set of RF antennas 1050 that are configured to generate RF pulses and to receive resulting MR signals from an object to which the RF pulses are directed. In one example, the RF antennas 1050 may be considered to correspond, at least in part, to element 510 (FIG. 5). In some examples, how the pulses are generated and how the resulting MR signals are received may be controlled, and thus may be selectively adapted, during an MRI procedure. Separate RF transmission and reception-coils can be employed. The RF antennas 1050 may be controlled, at least in part, by a set of RF transmission units 1060. An RF transmission unit 1060 may provide a signal to an amplifier 1062, which may manipulate the signal and provide a different signal to an RF antenna 1050. Unlike conventional systems, the amplifier 1062 may be a switched-mode current-source amplifier having gallium nitride FETs. The signal may be manipulated (e.g., amplified) using circuits described in connection with FIGS. 5-8, in FIG. 11, or in other ways.

The gradient coils supply 1040 and the RF transmission units 1060 may be controlled, at least in part, by a control computer 1070. In one example, the control computer 1070 may be programmed to perform methods like those described herein. The MR signals received from the RF antennas 1050 can be employed to generate an image, and thus may be subject to a transformation process like a two dimensional FFT that generates pixilated image data. The transformation can be performed by an image computer 1080 or other similar processing device. The image data may then be shown on a display 1099. While FIG. 10 illustrates an example MRI apparatus 1000 that includes various components connected in various ways, it is to be appreciated that other MRI apparatus, NMR apparatus, or MR apparatus may include other components connected in other ways.

In one example, MRI apparatus 1000 may include control computer 1070 and a digital controller operably connected to the amplifiers 1062. The amplifiers 1062 may include a set of LC-switched-mode coils operably connected to the digital controller. In one example, a member of the set of LC-switched-mode coils may be individually controllable by the control computer 1070. Additionally, the control computer 1070 may provide an LC-switched-mode coil with a digital control signal and the LC-switched-mode coil may output an analog RF signal based, at least in part, on the digital control signal.

In one example, the set of LC-switched-mode coils may be operably connected to the control computer 1070 by dedicated connections. The dedicated connections may include a copper cable, a fiber optic cable, a wireless connection, or other connections. In one example, an LC-switched-mode coil may be operably connected to a local memory that stores bit patterns that control production of the analog RF signal. Thus, the digital control signal may identify a stored bit pattern.

Figure 11:
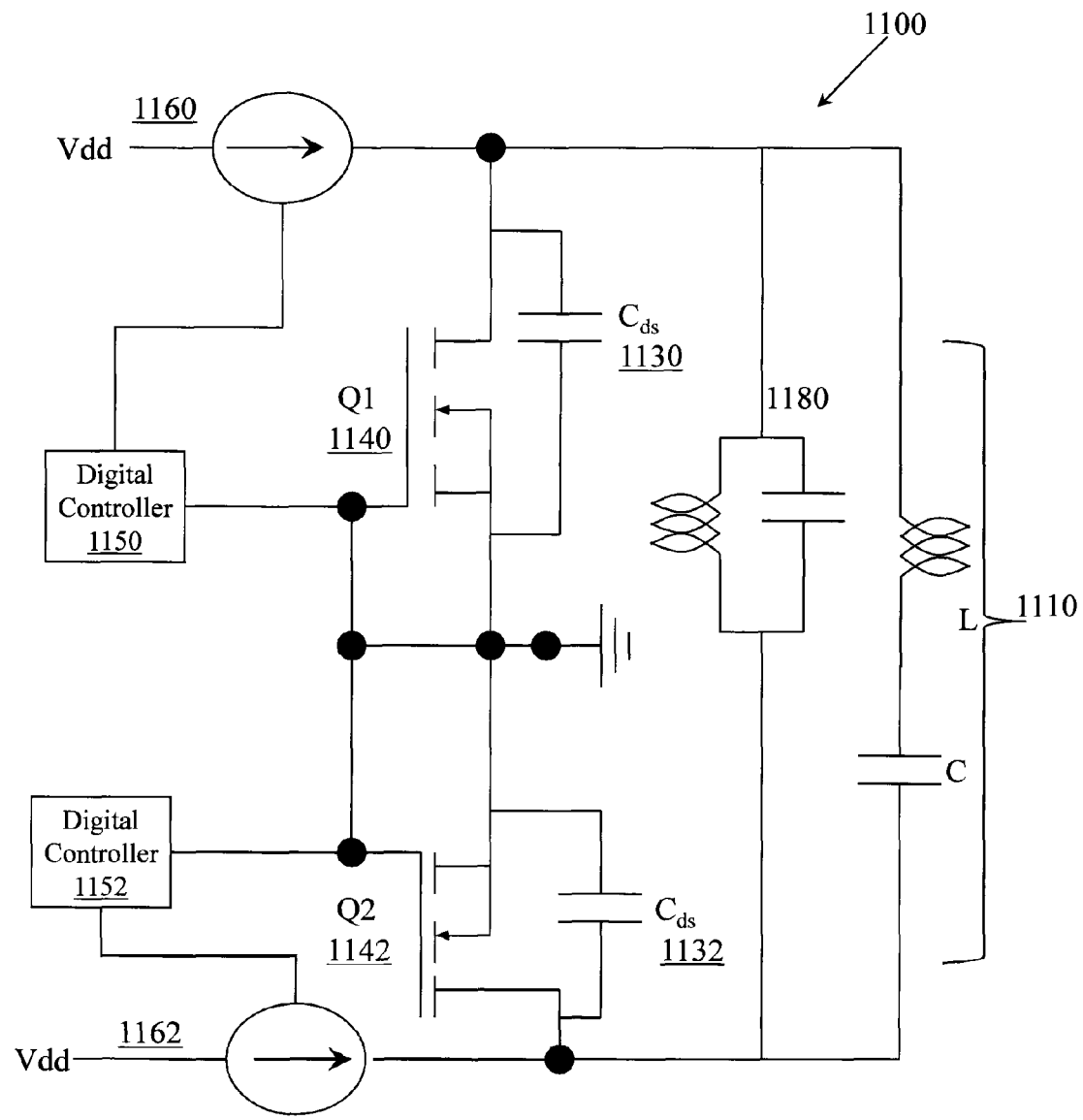
FIG. 11 illustrates a switched-mode current-source amplifier topology having a parallel resonance circuit portion.

FIG. 11 illustrates a CMCD amplifier topology 1100 having a parallel resonance circuit portion 1180. This resonance circuit 1180 is arranged in parallel with LC leg 1100. Resonance circuit 1180 facilitates conditioning and/or controlling a signal provided by topology 1100. Like other topologies described herein, topology 1100 includes several elements similar to those described in connection with topology 600 (FIG. 6). For example, topology 1100 includes an LC leg 1110, current-sources 1120 and 1122, drain-source capacitances 1130 and 1132, eGaN FETs 1140 and 1142, digital controllers 1150 and 1152, and generic current-sources 1160 and 1162, which are digitally controlled by digital controllers 1150 and 1152 respectively. Once again this digital control facilitates improving amplitude modulation accuracy and ease of use.

Figure 12:
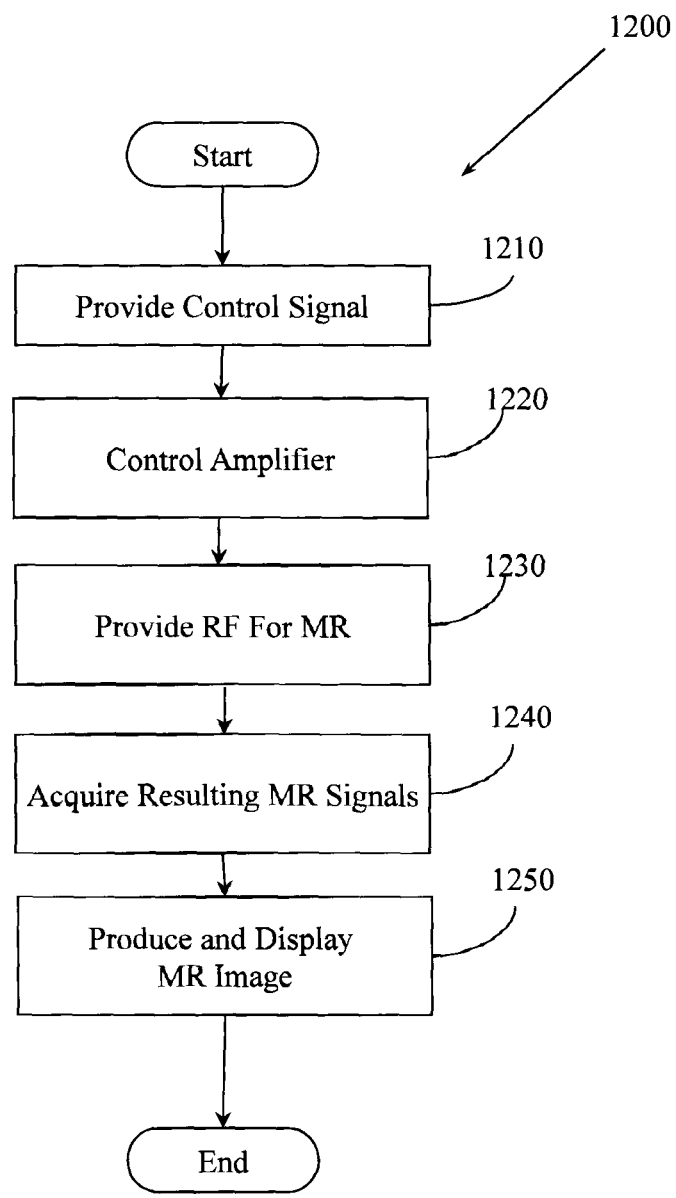
FIG. 12 illustrates a method associated with switched-mode current-source amplification.

FIG. 12 illustrates a method 1200 associated with controlling an on-coil switched-mode current-source amplifier. Method 1200 includes, at 1210, providing a voltage controlled signal to a gallium nitride field effect transistor based switched-mode current-source amplifier. The voltage controlled signal may be a low voltage (e.g., 5V) signal.

Method 1200 also includes, at 1220, controlling the amplifier to produce an amplified current as a function of the voltage controlled signal. Once the amplified current is available, it is provided to a transmit coil configured for use in parallel MRI.

Method 1200 also includes, at 1230, controlling the transmit coil to produce, as a function of the amplified current, RF energy suitable to produce MR in a material to which the RF energy is applied. For example the RF energy may be produced at wavelengths or frequencies that cause certain species (e.g., hydrogen) to resonate. Method 1200 also includes, at 1240, acquiring MR signals from the material to which the RF energy is applied. Once the resulting MR signals are acquired, method 1200 may proceed, at 1250, by producing and displaying an MR image.

Figure 13:
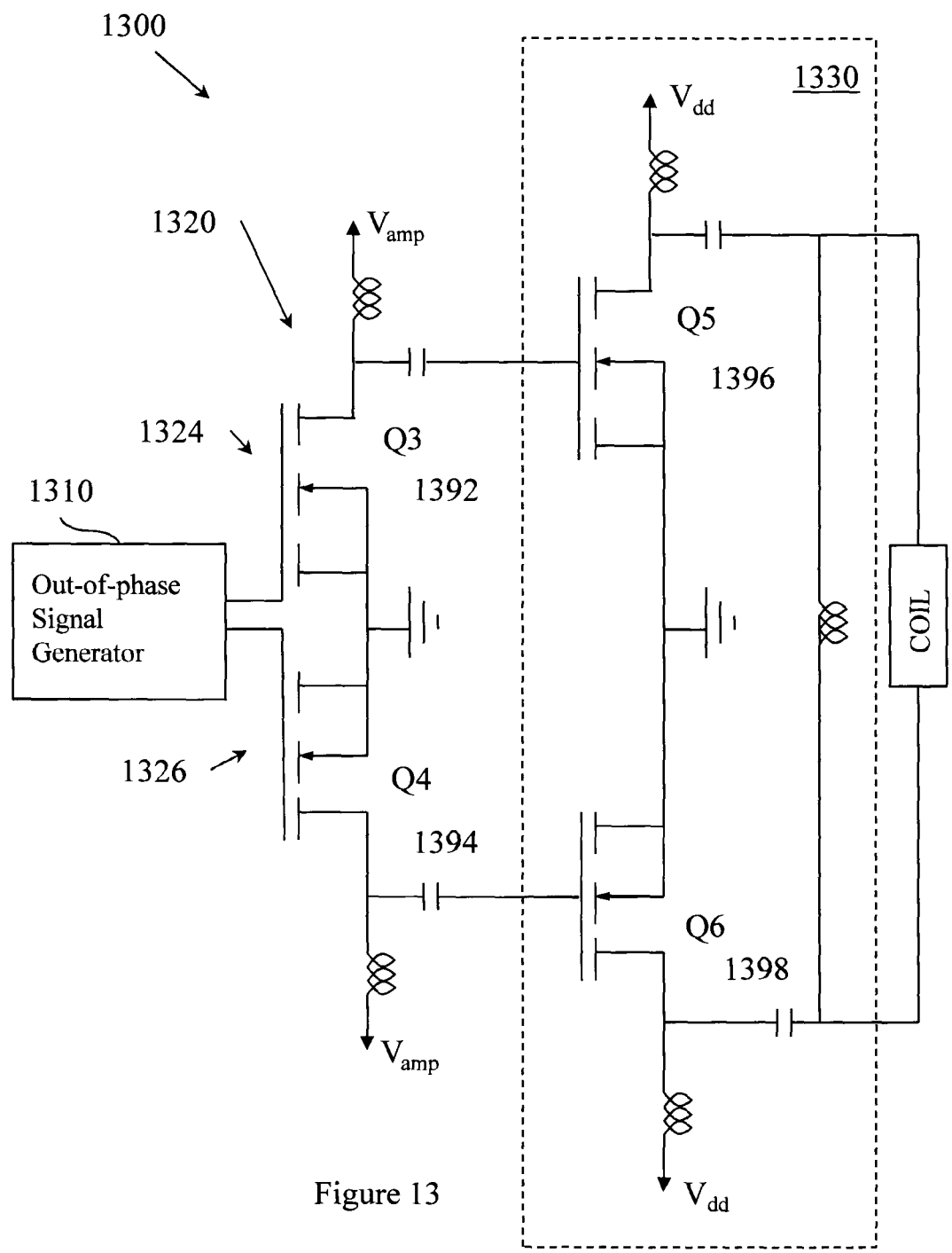
FIG. 13 illustrates an amplifier topology for use in parallel MR transmission including VMCD pre-amplifiers.

FIG. 13 illustrates an example CMCD topology 1300 that includes an out-of-phase signal generator 1310 and a switched voltage-mode class-D (VMCD) pre-amplification stage 1320 that pre-amplifies signals provided to an on-coil switched-mode current-source amplifier 1330. Amplifier 1330 may function as a CMCD amplifier. It can be seen that the on-coil amplifier 1330 is similar to the CMCD amplifier shown in FIG. 5 and includes two eGaN FETs Q5 1396, Q6 1398 that are driven by the output of the pre-amplification stage 1320.

The out-of-phase signal generator 1310 generates two out-of-phase RF signals and can be implemented in many ways. The pre-amplification stage 1320 includes first and second VMCD amplifiers 1324, 1326 that are configured to amplify one of the out-of-phase RF signals. In the described embodiment, the first and second VMCD amplifiers include eGaN FETs Q3 1392, Q4 1394. The first and second VMCD amplifiers 1324 and 1326 drive one of the FETs by selectively providing a pre-amplifier voltage ($V_{amp}$) to a gate of the driven FET. The switched-mode pre-amplification stage 1320 is configured to boost the out-of-phase RF signals from the out-of-phase signal generator 1310 to a voltage level that will efficiently switch the CMCD FETs.

Figure 14:
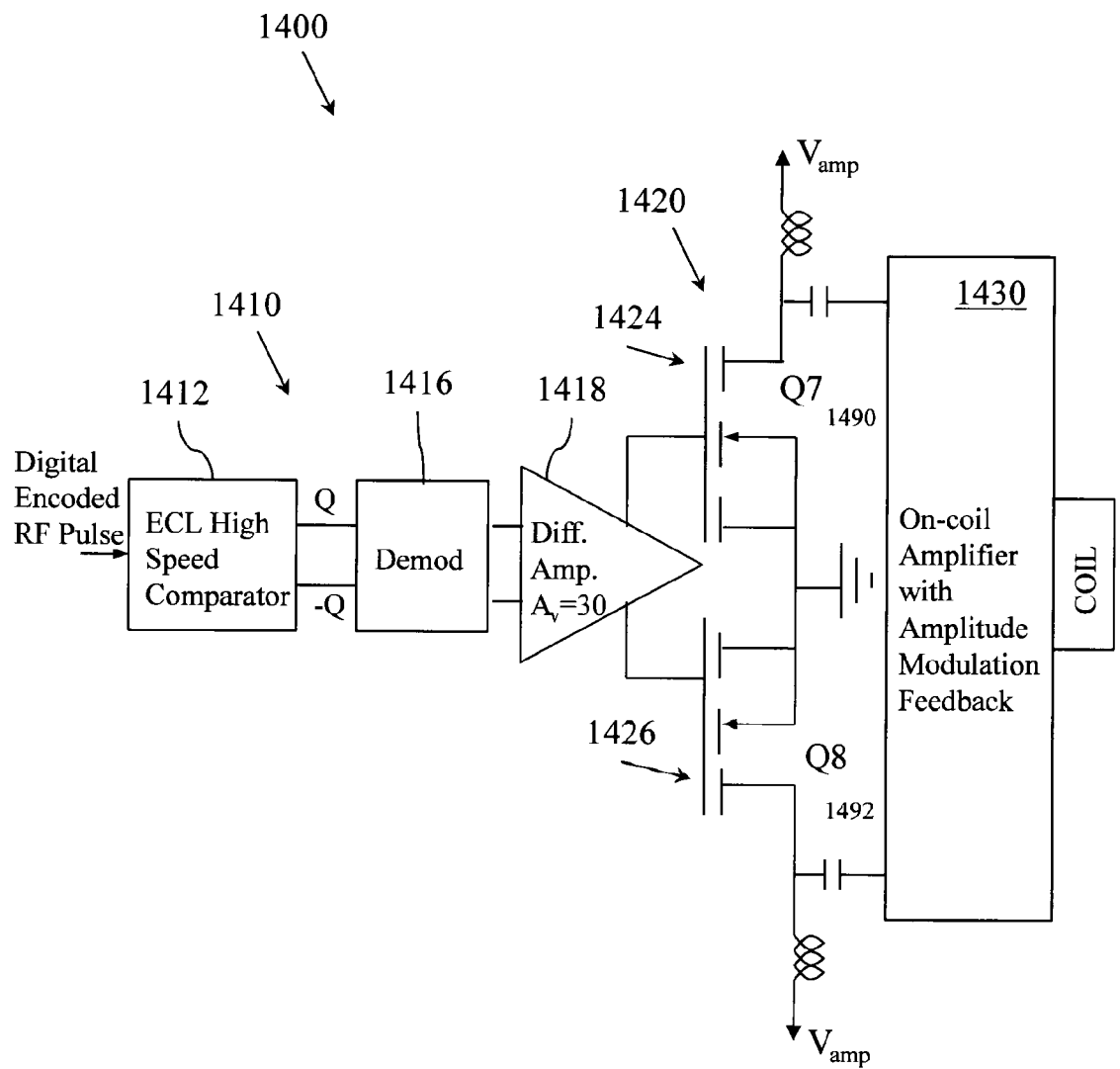
FIG. 14 illustrates an amplifier topology for use in parallel MR transmission including VMCD pre-amplifiers.

FIG. 14 illustrates a topology 1400 that includes a pre-amplification stage 1420 similar to the pre-amplification stage 1320 of FIG. 13. The pre-amplification stage 1420 includes first and second VMCD amplifiers 1424, 1426 that drive an on-coil switched-mode current-source amplifier 1430 similar to on-coil amplifier 1330 and shown schematically in block form for simplicity. The topology 1400 is configured to be driven by a digital encoded RF pulse. The encoded RF pulse is amplified and split into two out-of-phase signals (Q and −Q) through a high speed Emitter Coupled Logic (ECL) comparator 1412. The out-of-phase signals are demodulated through a band pass filter 1416 and further amplified through a differential amplifier 1418. The differential amplifier 1418 may include a cascade of high-speed differential amplifiers. The demodulated and amplified out-of-phase signals are further amplified by the pre-amplification stage 1420 and after pre-amplification have sufficient strength to drive the on-coil amplifier 1430.

In one embodiment, a 0.8V peak to peak digital encoded RF pulse is transformed through the pre-amplification stage (with a $V_{amp}$ of 28V) to a 55V peak to peak signal, which, in many instances, will be sufficient to efficiently switch the on-coil amplifier 1430. Due to the switched-mode operation of the pre-amplification stage 1420, the amplifier 1430 may need to include additional components to provide amplitude modulation for its output RF signal, as will be described in more detail below.

Figure 15:
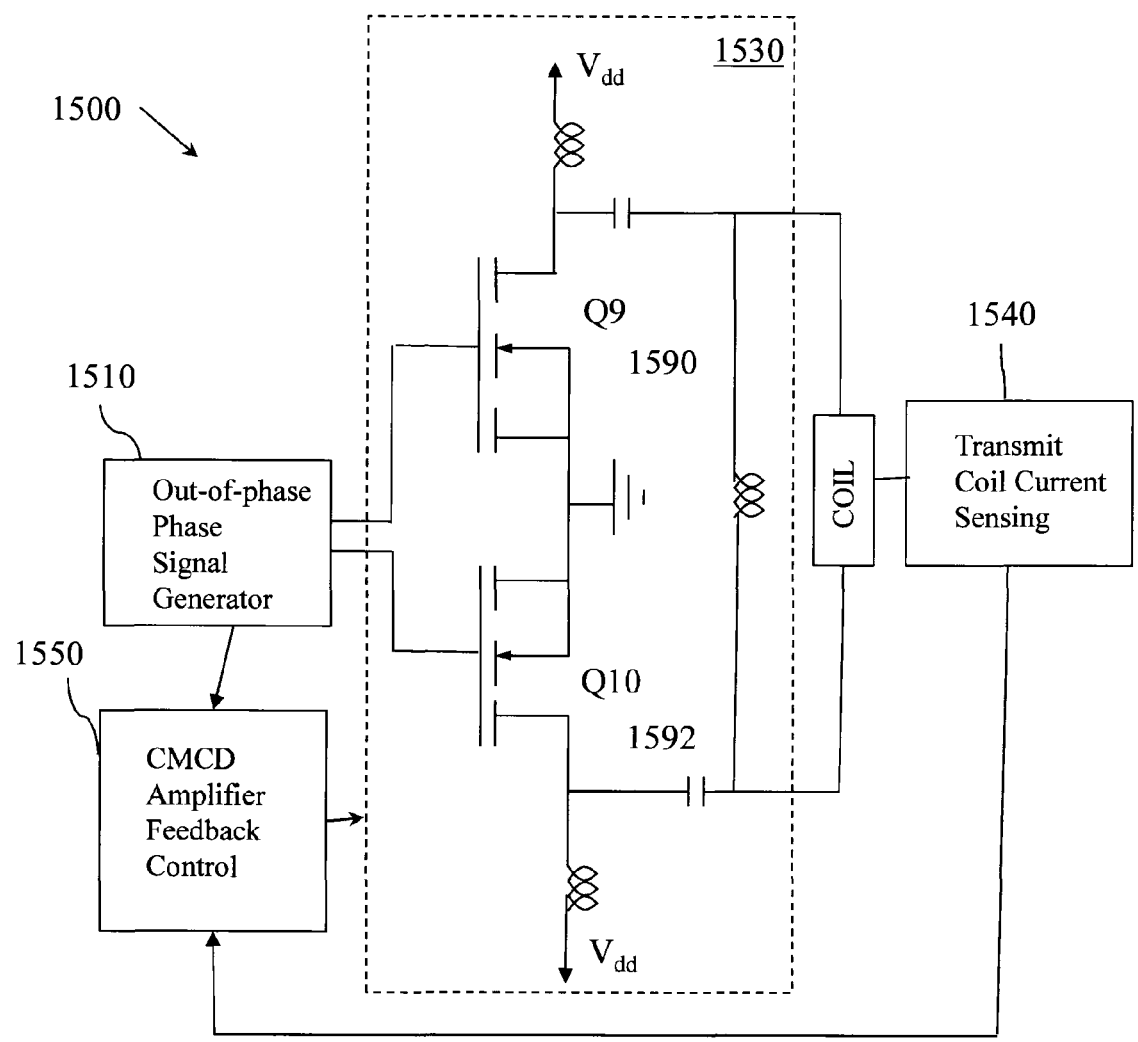
FIG. 15 illustrates an amplifier topology for use in parallel MR transmission including feedback control.

FIG. 15 illustrates a CMCD topology 1500 that includes an on-coil switched-mode current-source amplifier 1530 similar to amplifiers 1330 and 1430 (FIGS. 13 and 14). The amplifier 1530 includes an amplitude modulation system that uses feedback to modulate the amplitude of the RF signal output by the amplifier 1530. The amplifier 1530 is driven by an out-of-phase signal generator 1510 that provides switching voltages of sufficient strength to efficiently switch eGaN FETs Q9 1590 and Q10 1592. The signals from the out-of-phase signal generator 1510 are generated based on an input RF pulse having a desired frequency. To achieve sufficient switching voltages, the out-of-phase signal generator 1510 may include a pre-amplification stage similar to the pre-amplification stages 1320, 1420 (FIGS. 13 and 14) as well as a signal generator similar to the signal generator 1410 (FIG. 14).

The topology 1500 includes an amplifier feedback controller 1550 to modulate the amplitude of the output signal of the on-coil amplifier 1530. The feedback controller 1550 receives signals indicative of a transmit coil current from a transmit coil current sensing unit 1540. The feedback controller 1550 also receives signals indicative of the input RF pulse from the out-of-phase signal generator 1510. The feedback controller 1550 compares the signals indicative of the transmit coil current to the signals indicative of the input RF pulse and modulates an amplitude of the output of the amplifier 1530 based, at least in part, on this comparison.

Figure 16:
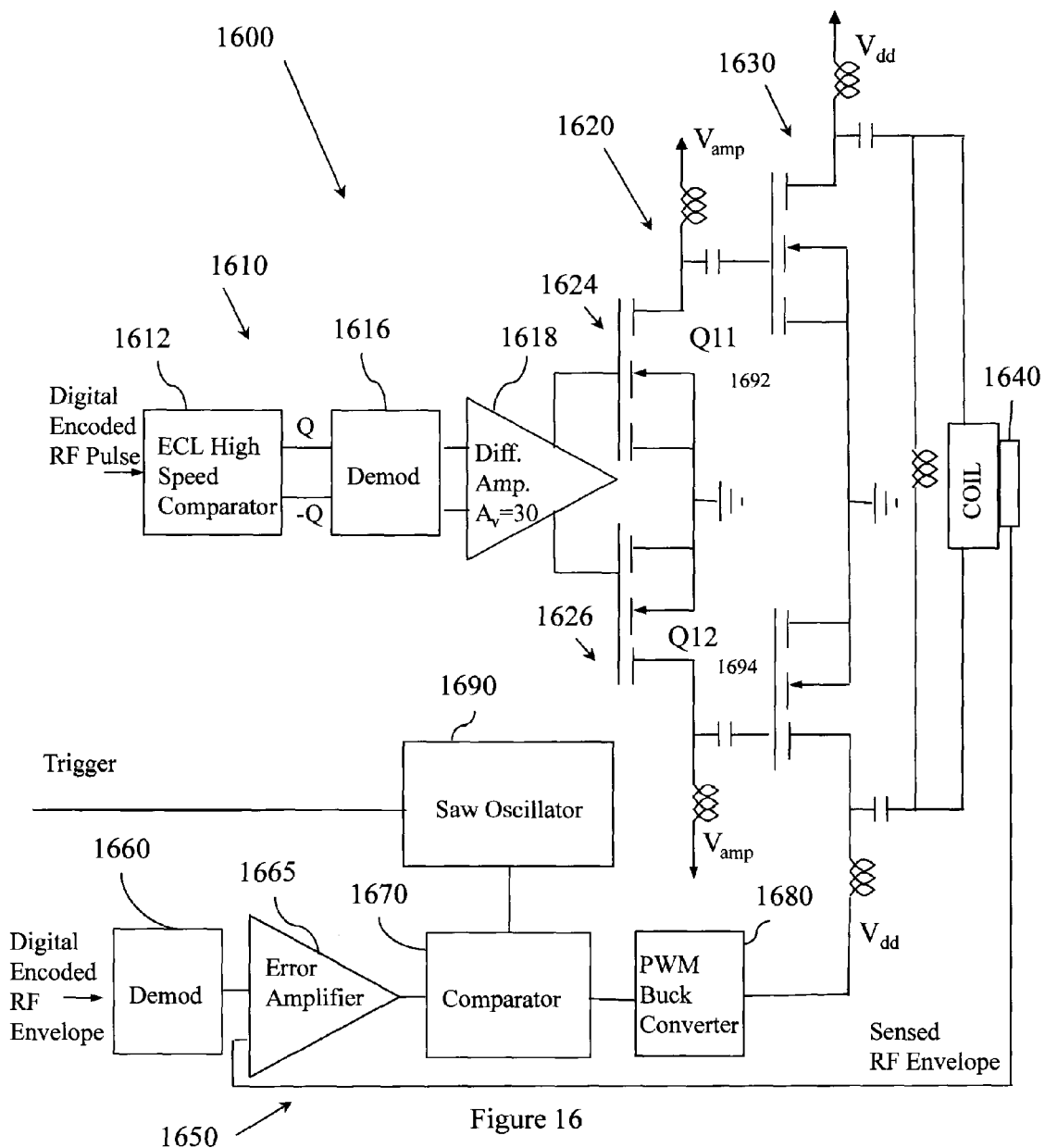
FIG. 16 illustrates an amplifier topology for use in parallel MR transmission including VMCD amplifiers and feedback control.

FIG. 16 illustrates a CMCD amplifier topology 1600 that includes an on-coil CMCD amplifier 1630 similar to amplifier 1530 (FIG. 15) and an out-of-phase signal generator 1610 and a VMCD pre-amplification stage 1620. The pre-amplification stage 1620 includes first and second VMCD amplifiers 1624, 1626 that drive an on-coil CMCD amplifier 1630.

The topology 1600 is configured to be driven by a digital encoded RF pulse. The encoded RF pulse is amplified and split into two out-of-phase signals (Q and −Q) through a high speed Emitter Coupled Logic (ECL) comparator 1612. The out-of-phase signals are demodulated through a band pass filter 1616 and further amplified through a differential amplifier 1618. The differential amplifier 1618 may include a cascade of high-speed differential amplifiers. The demodulated and amplified out-of-phase signals are further amplified by the pre-amplification stage 1620 and after pre-amplification have sufficient strength to drive the on-coil CMCD amplifier 1630. The FETs Q11 1692 and Q12 1694 may be eGaN FETs.

The topology 1600 includes a feedback controller 1650. The feedback controller 1650 modulates the amplitude of the output signal from the on-coil CMCD amplifier 1630 based on the envelope of the input digital encoded pulse as compared to the envelope of the current flowing in the transmit coil. The feedback controller 1650 includes a demodulator that demodulates a signal indicative of an envelope of the digital encoded RF pulse and inputs the envelope to an error amplifier 1665. A current envelope sensor 1640 is coupled to the transmit coil and provides an envelope of the transmit coil current to an error amplifier 1665. The current envelope sensor 1640 may be implemented by coupling a wire loop to the transmit coil and passing the demodulated signal through a low-pass filter with a cutoff frequency below the coil resonant frequency (e.g., 63.6 MHz at 1.5 T field strength). Other current envelope sensors may be employed.

An output of the error amplifier 1665 is provided to a comparator 1670. The comparator 1670 combines the output of the error amplifier 1665 with an output of a saw oscillator 1690 and thus acts as an oscillator to generate a pulse width modulated (PWM) signal based on the comparison of the input RF signal envelope and the envelope of the transmit coil current. This PWM signal is used to control a modified buck converter 1680 connected to the power stage for the CMCD amplifier 1630. The buck converter 1680 modulates the amplitude of the RF signal output by the CMCD amplifier 1630. A trigger signal is sent to the saw oscillator 1690 to avoid any false switching when no RF pulse is present. In this manner, the feedback controller 1650 modulates an amplitude of the output of the CMCD amplifier 1630 based, at least in part, on a comparison between envelopes of the input RF pulse and the transmit coil current. Sensing and comparing signal envelopes rather than sensing and comparing the signals themselves is less complex, which facilitates topology 1600 providing improved performance over other systems.

Figure 17:
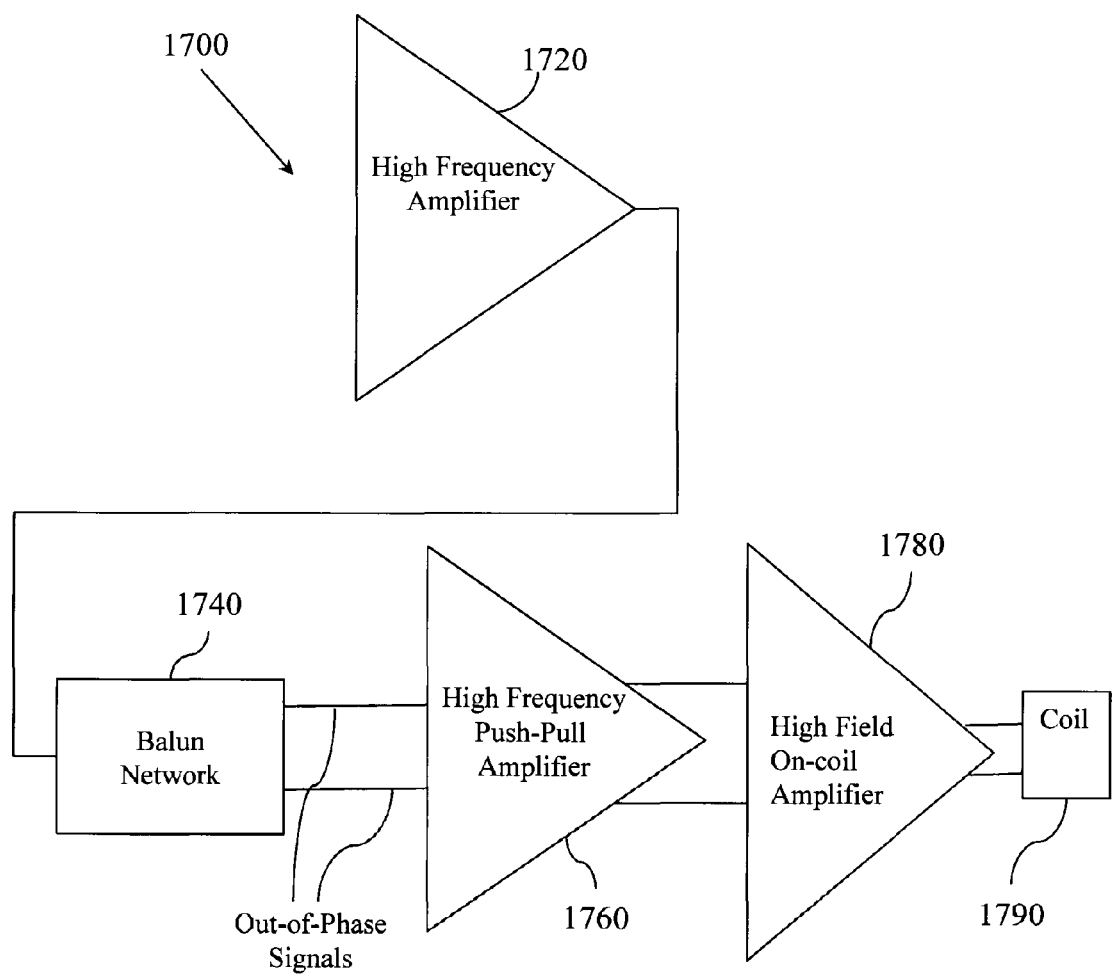
FIG. 17 illustrates an amplifier topology for use in high field parallel MR transmission.

FIG. 17 illustrates a schematic of a topology 1700 that is adapted for use with high field (e.g., 7 T) MRI systems that include an on-coil switched-mode current-source amplifier having eGaN FETs. The topology 1700 includes an RF signal generator (not shown) which may be digitally controlled. The RF signal generator generates a high frequency RF signal (e.g., 300 MHz). The output of the signal generator is amplified through a high frequency amplifier 1720.

The output of the high frequency amplifier 1720 is fed to a balun network 1740 that inputs the RF signal with respect to ground and converts the input RF signal into a pair of first and second balanced out-of-phase signals, with respect to ground, at the high frequency. The balun network 1740 can be implemented with types of networks that convert a single input voltage with respect to ground into two balanced 180 degree out-of-phase signals (e.g., wound wire transformers, wavelength-related lengths of transmission line).

The balun network 1740 may be implemented using a quarter-wavelength transmission line that has a length substantially equal to an integer multiple of one quarter of the wavelength of the RF signal generated by the signal generator (e.g., $n(\lambda)/4$, where n is an integer). The quarter-wavelength transmission line converts the input RF signal into balanced 180 degree out-of-phase signals. In high-field MRIs where the RF signal will have shorter wavelengths (e.g., approximately 70 cm at 7 T), it becomes feasible to employ a quarter-wavelength transmission line (e.g., 17.5 cm) to generate the out-of-phase signals that are ultimately utilized to drive the on-coil switched-mode amplifier. While the length of the transmission line would necessarily be longer in lower field strengths, it should be understood by one of skill in art that MRI systems operating with lower magnetic field strengths may also employ the balun network 1740 implemented using a quarter-wavelength transmission line. The out-of-phase signals are amplified by a high frequency push-pull amplifier 1760 before being provided to a high field on-coil CMCD amplifier 1780 that may be adapted for use in a high field environment.

Figure 18:
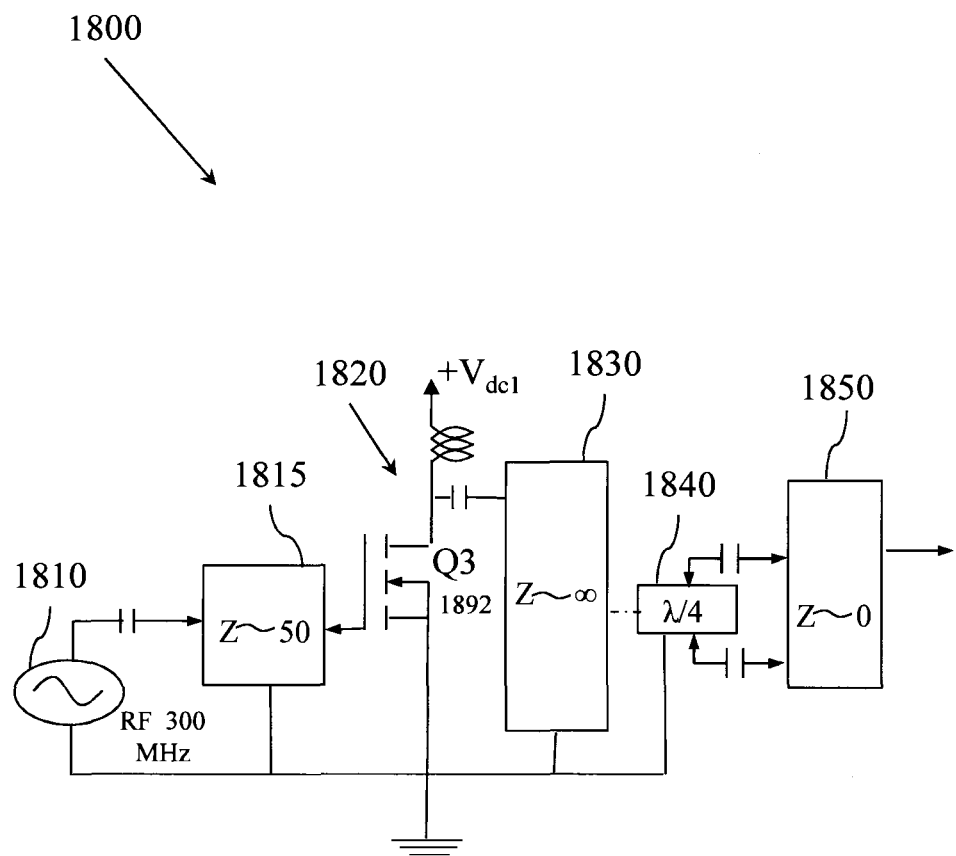
FIG. 18 illustrates a first portion of an amplifier topology for use in high field parallel MR transmission.
Figure 19:
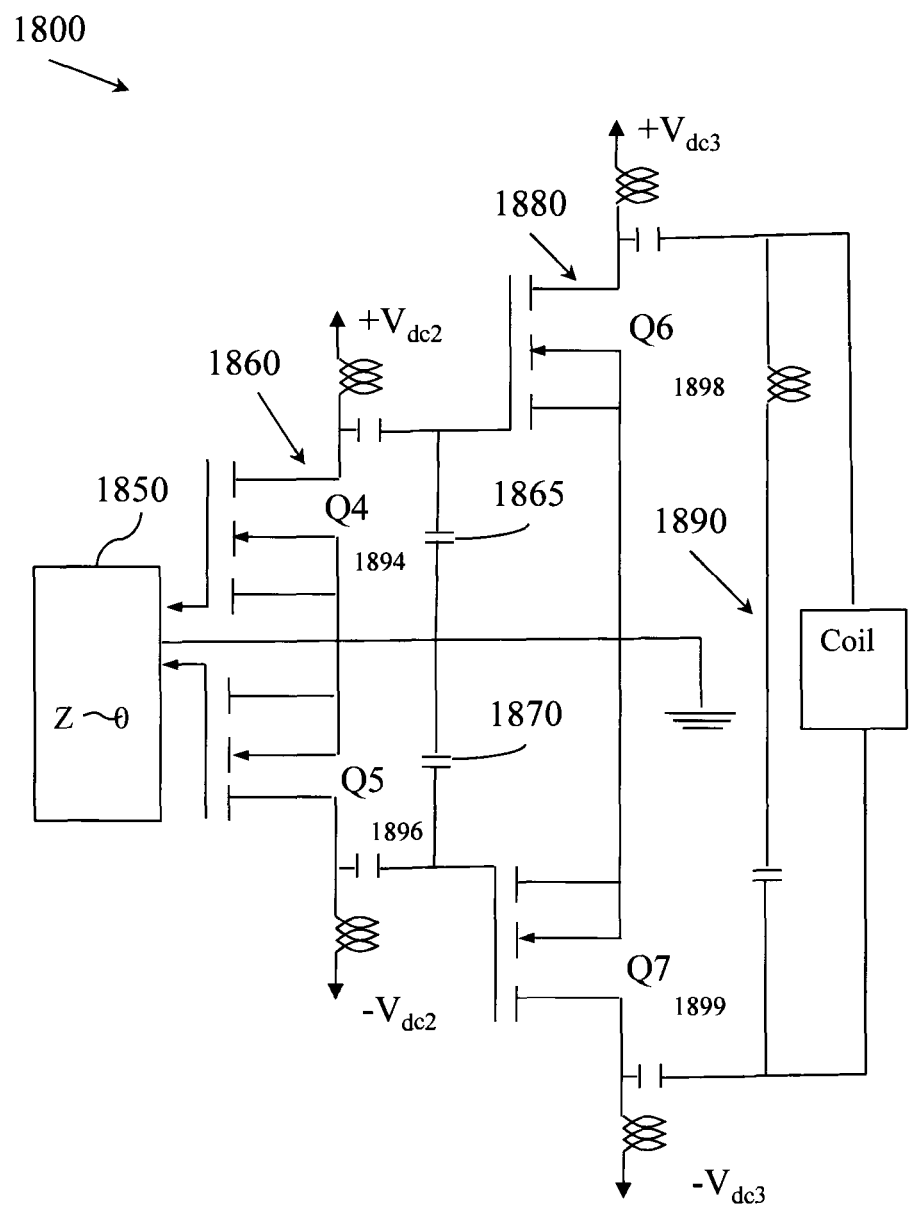
FIG. 19 illustrates a second portion of an amplifier topology for use in high field parallel MR transmission.

FIGS. 18 and 19 illustrate a more detailed schematic of an example topology 1800 that is adapted for use with 7 T field MRI systems that include an on-coil switched-mode current-source amplifier having eGaN FETs. The topology 1800 includes a 300 MHz RF signal generator 1810 coupled to a 50 ohm impedance matching network 1815. A class A amplifier 1820 amplifies the RF signal. In the illustrated topology, the class A amplifier is implemented with an eGaN FET Q3 1892 that is connected at its drain to a first DC voltage $V_{dc1}$ and driven by the RF signal applied at its gate. The amplified RF signal is input to a balun network that includes a quarter-wavelength transmission line 1840.

The quarter-wavelength transmission line 1840 may be implemented using a semi-rigid length of coaxial cable having a length that is equal to an integer multiple of one quarter of the wavelength of the RF signal. An inner conductor of the coaxial cable is connected to the RF signal at the input and a first conductor at the output. An outer shield layer of the coaxial cable is grounded at the input and is connected to a second conductor at the output. The first and second conductors provide the out-of-phase signals with respect to ground. The resulting quarter-wavelength transmission line thus functions as a balun and produces two balanced, out-of-phase signals. Impedance matching networks 1830 and 1850 can be designed to minimize power losses through the quarter-wavelength transmission line 1840.

In the illustrated topology, the balanced, out-of-phase signals output by the quarter-wavelength transmission line 1840 drive a class B push-pull amplifier 1860 that boosts the peak voltage of the signal to a voltage $V_{dc2}$ that is sufficient to efficiently switch an on-coil CMCD amplifier 1880. The push-pull amplifier 1860 includes two eGaN FETs Q4 1894 and Q5 1896 connected in a common source arrangement with drains connected to gates of eGaN FETs Q6 1898 and Q7 1899 that are part of the on-coil amplifier 1880.

The topology 1800 includes components configured to optimize performance in high field strength applications. For example capacitors 1865 and 1870 connected between the gate and source of the eGaN FETs Q6 1898 and Q7 1899 are configured to match impedance to higher values and avoid a dramatic loss of gain from the push-pull amplifier 1860. An LC filter 1890 is disposed in parallel between the on-coil CMCD amplifier 1880 and the transmit coil. The LC filter 1890 is configured to resonate with the parasitic impedance generated by the FETs Q6 1898 and Q7 1899 operating at 300 MHz to attenuate harmonics that are typically present with switched-mode amplifiers. The LC filter 1890 also provides decoupling from transmitting neighboring coils due to the high impedance seen from the coil at higher frequencies. While the topology 1800 is described in connection with a high field strength MRI, it will be apparent to one of skill in the art that one or more the various illustrated circuit components may also be advantageously employed with respect to MR equipment of other field strengths.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

To the extent that the term "includes" or "including" is employed in the detailed description or the claims, it is intended to be inclusive in a manner similar to the term "comprising" as that term is interpreted when employed as a transitional word in a claim.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

Although the subject matter has been described in language specific to structural features or methodological acts, it is to be understood that the subject matter defined in the appended claims is not necessarily limited to the specific features or acts described above. Rather, the specific features and acts described above are disclosed as example forms of implementing the claims.

What is claimed is:

1. An on-coil switched-mode current-source amplifier for parallel transmission in magnetic resonance (MR), comprising:
    at least two field effect transistors (FETs) connected by a coil including an LC (inductance-capacitance) leg, the at least two FETs being gallium nitride (GaN) FETs,
    a class S amplifier configured to provide a source voltage to the at least two FETs,
    where the coil is configured to produce an output analog radio frequency (RF) signal associated with parallel magnetic resonance imaging (MRI) transmission, and
    where the output analog RF signal depends, at least in part, on a current output by the at least two FETs.

2. The on-coil switched-mode current-source amplifier of claim 1, the at least two FETs being enhanced mode gallium nitride (eGaN) FETs.

3. The on-coil switched-mode current-source amplifier of claim 1, where the at least two FETs drive a current in the coil of at least 3 A rms.

4. The on-coil switched-mode current-source amplifier of claim 1, where one of the at least two FETs is less than 2 $mm^2$.

5. The on-coil switched-mode current-source amplifier of claim 1, where the amplifier is configured to be within 1 centimeter of a bore of an MR apparatus.

6. The on-coil switched-mode current-source amplifier of claim 1, the coil being a multi-turn coil.

7. The on-coil switched-mode current-source amplifier of claim 1, where a drain efficiency of the at least two FETs is at least 85% when driving a 50 ohm load.

8. The on-coil switched-mode current-source amplifier of claim 1, where a power added efficiency of the at least two FETs is at least 85% when driving a 50 ohm load.

9. The on-coil switched-mode current-source amplifier of claim 1, comprising:
    an envelope elimination and restoration circuit configured to replicate shaped RF pulses produced by an MR scanner, the envelope elimination and restoration circuit connected to the on-coil switched-mode current-source amplifier.

10. The on-coil switched-mode current-source amplifier of claim 1, where the at least two FETs drive a current in the coil of at least 5 A rms.

11. The on-coil switched-mode current-source amplifier of claim 1, where one of the at least two FETs is less than 0.5 $mm^2$.

12. The on-coil switched-mode current-source amplifier of claim 1, where the amplifier is configured to be within 2 meters of a bore of an MR apparatus.

13. An on-coil switched-mode current-source amplifier for parallel transmission in magnetic resonance (MR), comprising:
    at least two field effect transistors (FETs) connected by a coil including an LC (inductance-capacitance) leg, the at least two FETs being gallium nitride (GaN) FETs,
    a class S amplifier configured to provide a source voltage to the at least two FETs, where the coil is configured to produce an output analog radio frequency (RF) signal associated with parallel magnetic resonance imaging (MRI) transmission, a current detector that detects the current output by the coil as controlled, at least in part, by the at least two FETs, and where the output analog RF signal depends, at least in part, on a current output by the at least two FETs.

14. The on-coil switched-mode current-source amplifier of claim 13, the at least two FETs being enhanced mode gallium nitride (eGaN) FETs.

15. The on-coil switched-mode current-source amplifier of claim 13, where the at least two FETs drive a current in the coil of at least 3 A rms.

16. The on-coil switched-mode current-source amplifier of claim 13, where one of the at least two FETs is less than 2 mm$^2$.

17. The on-coil switched-mode current-source amplifier of claim 13, where the amplifier is configured to be within 1 centimeter of a bore of an MR apparatus.

18. The on-coil switched-mode current-source amplifier of claim 13, comprising:

an envelope elimination and restoration circuit configured to replicate shaped RF pulses produced by an MR scanner, the envelope elimination and restoration circuit connected to the on-coil switched-mode current-source amplifier.

19. The on-coil switched-mode current-source amplifier of claim 13, where the at least two FETs drive a current in the coil of at least 5 A rms.

20. The on-coil switched-mode current-source amplifier of claim 13, where one of the at least two FETs is less than 0.5 mm$^2$.

21. The on-coil switched-mode current-source amplifier of claim 13, where the amplifier is configured to be within 2 meters of a bore of an MR apparatus.

22. An on-coil switched-mode current-source amplifier for parallel transmission in magnetic resonance (MR), comprising:

at least two field effect transistors (FETs) connected by a coil including an LC (inductance-capacitance) leg, the at least two FETs being gallium nitride (GaN) FETs, a class S amplifier configured to provide a source voltage to the at least two FETs, where the coil is configured to produce an output analog radio frequency (RF) signal associated with parallel magnetic resonance imaging (MRI) transmission, a current detector that detects the current output by the coil as controlled, at least in part, by the at least two FETs, where the output analog RF signal depends, at least in part, on a current output by the at least two FETs, and where the class S amplifier controls the source voltage provided to the at least two FETs as a function of the current detected by the current detector.

23. The on-coil switched-mode current-source amplifier of claim 22, the at least two FETs being enhanced mode gallium nitride (eGaN) FETs.

24. The on-coil switched-mode current-source amplifier of claim 22, where the at least two FETs drive a current in the coil of at least 3 A rms.

25. The on-coil switched-mode current-source amplifier of claim 22, where one of the at least two FETs is less than 2 mm$^2$.

26. The on-coil switched-mode current-source amplifier of claim 22, where the amplifier is configured to be within 1 centimeter of a bore of an MR apparatus.

27. The on-coil switched-mode current-source amplifier of claim 22, comprising:

an envelope elimination and restoration circuit configured to replicate shaped RF pulses produced by an MR scanner, the envelope elimination and restoration circuit connected to the on-coil switched-mode current-source amplifier.

28. The on-coil switched-mode current-source amplifier of claim 22, where the at least two FETs drive a current in the coil of at least 5 A rms.

29. The on-coil switched-mode current-source amplifier of claim 22, where one of the at least two FETs is less than 0.5 mm$^2$.

30. The on-coil switched-mode current-source amplifier of claim 22, where the amplifier is configured to be within 2 meters of a bore of an MR apparatus.

31. An on-coil switched-mode current-source amplifier for parallel transmission in magnetic resonance (MR), comprising:

at least two field effect transistors (FETs) connected by a coil including an LC (inductance-capacitance) leg, the at least two FETs being gallium nitride (GaN) FETs, where the coil is configured to produce an output analog radio frequency (RF) signal associated with parallel magnetic resonance imaging (MRI) transmission, where the output analog RF signal depends, at least in part, on a current output by the at least two FETs, and where a drain efficiency of the at least two FETs is at least 85% when driving a 50 ohm load.

32. The on-coil switched-mode current-source amplifier of claim 31, the at least two FETs being enhanced mode gallium nitride (eGaN) FETs.

33. The on-coil switched-mode current-source amplifier of claim 31, where the at least two FETs drive a current in the coil of at least 3 A rms.

34. The on-coil switched-mode current-source amplifier of claim 31, where one of the at least two FETs is less than 2 mm$^2$.

35. The on-coil switched-mode current-source amplifier of claim 31, where the amplifier is configured to be within 1 centimeter of a bore of an MR apparatus.

36. The on-coil switched-mode current-source amplifier of claim 31, comprising:

an envelope elimination and restoration circuit configured to replicate shaped RF pulses produced by an MR scanner, the envelope elimination and restoration circuit connected to the on-coil switched-mode current-source amplifier.

37. The on-coil switched-mode current-source amplifier of claim 31, where the at least two FETs drive a current in the coil of at least 5 A rms.

38. The on-coil switched-mode current-source amplifier of claim 31, where one of the at least two FETs is less than 0.5 mm$^2$.

39. The on-coil switched-mode current-source amplifier of claim 31, where the amplifier is configured to be within 2 meters of a bore of an MR apparatus.

40. An on-coil switched-mode current-source amplifier for parallel transmission in magnetic resonance (MR), comprising:

at least two field effect transistors (FETs) connected by a coil including an LC (inductance-capacitance) leg, the at least two FETs being gallium nitride (GaN) FETs, where the coil is configured to produce an output analog radio frequency (RF) signal associated with parallel magnetic resonance imaging (MRI) transmission, where the output analog RF signal depends, at least in part, on a current output by the at least two FETs, and where a power added efficiency of the at least two FETs is at least 85% when driving a 50 ohm load.

41. The on-coil switched-mode current-source amplifier of claim 40, the at least two FETs being enhanced mode gallium nitride (eGaN) FETs.

42. The on-coil switched-mode current-source amplifier of claim 40, where the at least two FETs drive a current in the coil of at least 3 A rms.

43. The on-coil switched-mode current-source amplifier of claim 40, where the at least two FETs is one of less than 2 mm$^2$.

44. The on-coil switched-mode current-source amplifier of claim 40, where the amplifier is configured to be within 1 centimeter of a bore of an MR apparatus.

45. The on-coil switched-mode current-source amplifier of claim 40, comprising:
an envelope elimination and restoration circuit configured to replicate shaped RF pulses produced by an MR scanner, the envelope elimination and restoration circuit connected to the on-coil switched-mode current-source amplifier.

46. The on-coil switched-mode current-source amplifier of claim 40, where the at least two FETs drive a current in the coil of at least 5 A rms.

47. The on-coil switched-mode current-source amplifier of claim 40, where one of the at least two FETs is less than 0.5 mm$^2$.

48. The on-coil switched-mode current-source amplifier of claim 40, where the amplifier is configured to be within 2 meters of a bore of an MR apparatus.

49. An on-coil switched-mode current-source amplifier for parallel transmission in magnetic resonance (MR), comprising:
at least two field effect transistors (FETs) connected by a coil including an LC (inductance-capacitance) leg, the at least two FETs being gallium nitride (GaN) FETs,
a class S amplifier configured to provide a source voltage to the at least two FETs, where the coil is configured to produce an output analog radio frequency (RF) signal associated with parallel magnetic resonance imaging (MRI) transmission,
a current detector that detects the current output by the coil as controlled, at least in part, by the at least two FETs,
where the output analog RF signal depends, at least in part, on a current output by the at least two FETs,
where the class S amplifier controls the source voltage provided to the at least two FETs as a function of the current detected by the current detector, and
where the efficiency of the class S amplifier is at least 90%.

50. The on-coil switched-mode current-source amplifier of claim 49, the at least two FETs being enhanced mode gallium nitride (eGaN) FETs.

51. The on-coil switched-mode current-source amplifier of claim 45, where the at least two FETs drive a current in the coil of at least 3 A rms.

52. The on-coil switched-mode current-source amplifier of claim 49, where one of the at least two FETs is less than 2 mm$^2$.

53. The on-coil switched-mode current-source amplifier of claim 49, where the amplifier is configured to be within 1 centimeter of a bore of an MR apparatus.

54. The on-coil switched-mode current-source amplifier of claim 49, comprising:
an envelope elimination and restoration circuit configured to replicate shaped RF pulses produced by an MR scanner, the envelope elimination and restoration circuit connected to the on-coil switched-mode current-source amplifier.

55. The on-coil switched-mode current-source amplifier of claim 49, where the at least two FETs drive a current in the coil of at least 5 A rms.

56. The on-coil switched-mode current-source amplifier of claim 49, where one of the at least two FETs is less than 0.5 mm$^2$.

57. The on-coil switched-mode current-source amplifier of claim 49, where the amplifier is configured to be within 2 meters of a bore of an MR apparatus.

\* \* \* \* \*

UNITED STATES PATENT AND TRADEMARK OFFICE
CERTIFICATE OF CORRECTION

PATENT NO. : 9,747,789 B2  
APPLICATION NO. : 14/053144  
DATED : August 29, 2017  
INVENTOR(S) : Griswold et al.

Page 1 of 1

It is certified that error appears in the above-identified patent and that said Letters Patent is hereby corrected as shown below:

Column 17, Claim 43, Line 10, "where the" should be --where one of the--.

Column 17, Claim 43, Line 10, "is one of less" should be --is less--.

Signed and Sealed this
Twentieth Day of March, 2018

Andrei Iancu
*Director of the United States Patent and Trademark Office*